United States Patent [19]
Hochman et al.

[11] Patent Number: 5,465,718
[45] Date of Patent: Nov. 14, 1995

[54] SOLID TUMOR, CORTICAL FUNCTION, AND NERVE TISSUE IMAGING METHODS AND DEVICE

[76] Inventors: Daryl Hochman, 22933 Edmonds Way, Edmonds, Wash. 98020; Michael M. Haglund, 1647 N. 197th Pl., Seattle, Wash. 98133

[21] Appl. No.: 73,353

[22] Filed: Jun. 7, 1993

Related U.S. Application Data

[63] Continuation-in-part of Ser. No. 894,270, Jun. 8, 1992, which is a continuation-in-part of Ser. No. 565,454, Aug. 10, 1990, Pat. No. 5,215,095.

[51] Int. Cl.$^6$ .............................. A61B 5/00; G01N 21/00
[52] U.S. Cl. ...................... 128/653.1; 128/654; 128/664; 128/665; 128/741; 348/68; 348/77; 348/164; 364/413.13
[58] Field of Search ................................ 128/633, 653.1, 128/664, 665, 741, 654; 382/6; 358/98, 110, 111, 113; 364/413.13; 348/65, 68, 69, 77, 162, 164

[56] References Cited

U.S. PATENT DOCUMENTS

| | | | |
|---|---|---|---|
| 4,541,438 | 9/1985 | Parker et al. | 128/664 |
| 4,930,516 | 6/1990 | Alfano et al. | 128/665 |
| 5,119,815 | 6/1992 | Chance | 128/665 |
| 5,185,809 | 2/1993 | Kennedy et al. | 128/653.1 |
| 5,198,977 | 3/1993 | Salb | 128/633 |
| 5,200,345 | 4/1993 | Young | 128/653.1 |
| 5,215,095 | 6/1993 | Macvicar et al. | 128/665 |
| 5,284,154 | 2/1994 | Raymond et al. | 128/741 |

OTHER PUBLICATIONS

Herbin et al., "Automated Registration of Dissimilar Images: Application to Medical Imagery", pp. 77–88, 1989.
Grinvald et al., "High–Resolution Optical Imaging of Functional Brain Architecture in the Awake Monkey", pp. 11559–11563, 1991; Proc. Nat'l Acad. Sci. USA.
Grinvald et al., "Optical Imaging of Neuronal Activity", Physiological Reviews, vol. 68, No. 4, pp. 1285–1366, 1988.
McCormick et al., "Intracerebral Penetration of Infrared Light", J. Neurosurg., vol. 76, pp. 315–318, Feb. 1992.
Chance et al. Proc. Natl. Acad. Sci. USA, 90:3423, 1993, "Highly Sensitive Object Location in Tissue Models".
D'Orsi et al., in L. W. Bassett and R. H. Gold eds., Breast Cancer Detection, Mammography and Other Methods in Breast Imaging, 2nd ed., Grune & Stratton, Inc., 1987; pp. 169–177.
Ts'o et al., Science 249:417, 1990.
Frostig et al., Proc. Natl. Acad. Sci. USA 87:6082, 1990; "Cortical Functional Architecture and Local Coupling Between Neuronal Activity and the Microcirculation Revealed by in vivo High–Resolution Optical Imaging".
Haglund and Blasdel, "Video Imaging of Neuronal Activity"; pp. 85–111, undated.

*Primary Examiner*—Krista M. Pfaffle

[57] ABSTRACT

There is disclosed a method for imaging tumor tissue adjacent to nerve tissue to aid in selective resection of tumor tissue without destroying nerve tissue, comprising the steps of illuminating an area of interest with a source of electromagnetic radiation (emr) containing wavelengths absorbed by a dye, obtaining a video signal of the area of interest as a series of frames and processing the series of frames into an averaged control image, stimulating the nerve with an appropriate paradigm to activate the nerve, obtaining a nerve subsequent series of frames at the time of stimulation and processing the nerve subsequent series of frames into a nerve subsequent averaged image, obtaining a nerve difference image by subtracting the averaged control image from the nerve subsequent averaged image to image the active nerve, administering the dye into vasculature perfusing the area of interest, obtaining a subsequent series of frames and processing the tumor subsequent series of frames into a tumor subsequent averaged image, and obtaining a tumor difference image by subtracting the averaged control image from the tumor subsequent averaged image to visualize the tumor.

4 Claims, 20 Drawing Sheets

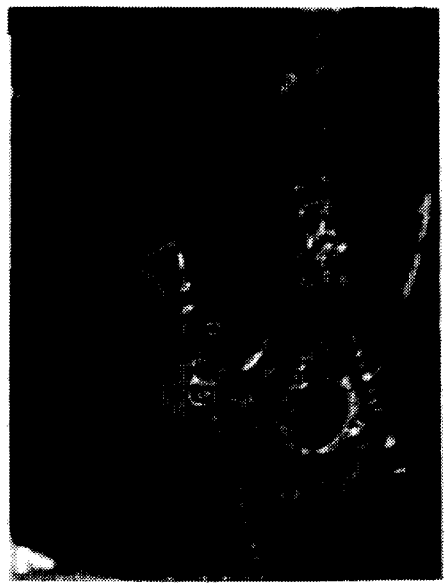
FIGURE 2C2
FIGURE 2C4
FIGURE 2B2
FIGURE 2B4
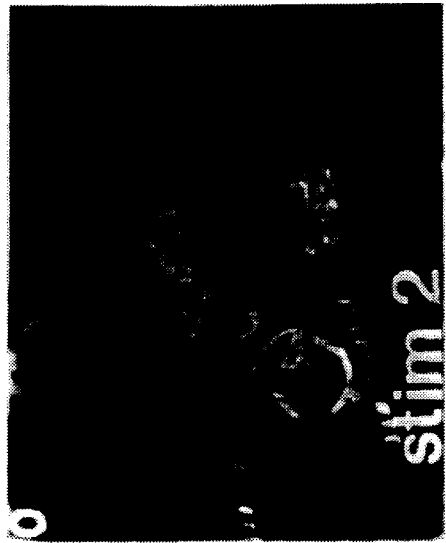
FIGURE 2A2
FIGURE 2A4

FIGURE 3A
FIGURE 3B
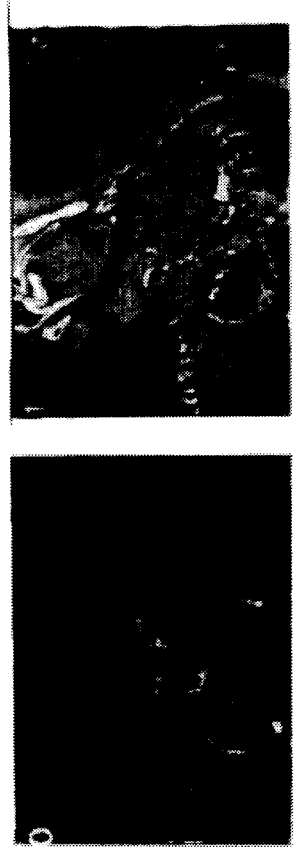
FIGURE 3C
FIGURE 3D
FIGURE 3E
FIGURE 3F
FIGURE 3G
FIGURE 3H

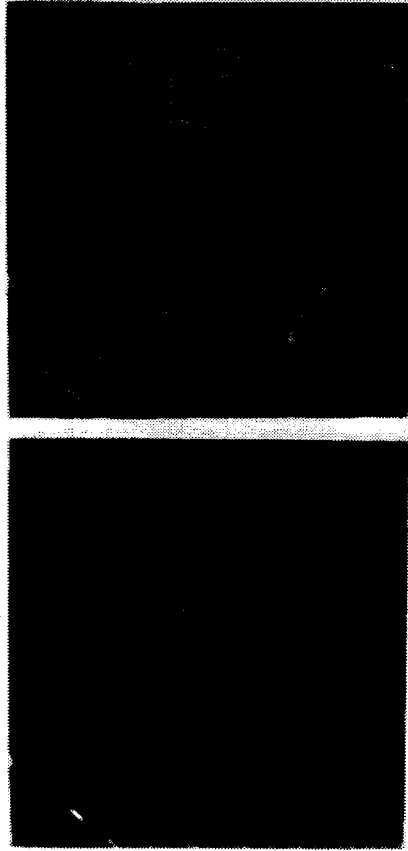
FIGURE 4A FIGURE 4B FIGURE 4C FIGURE 4D
FIGURE 4E FIGURE 4F FIGURE 4G FIGURE 4H

FIGURE 5C
FIGURE 5B
FIGURE 5A

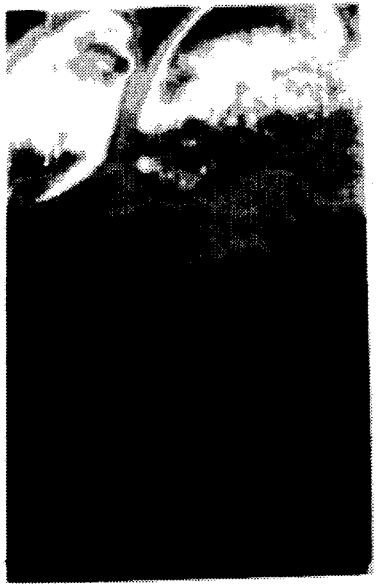
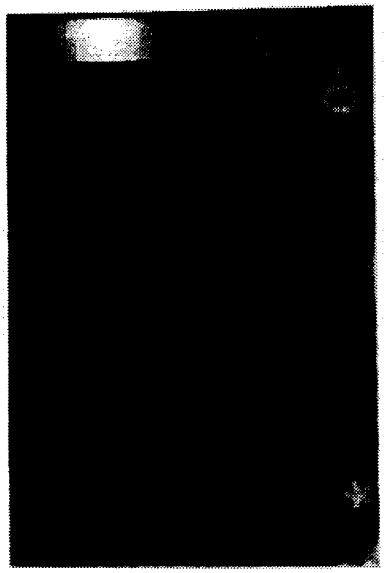
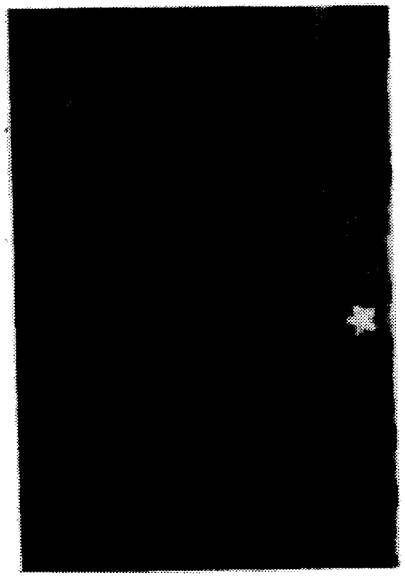
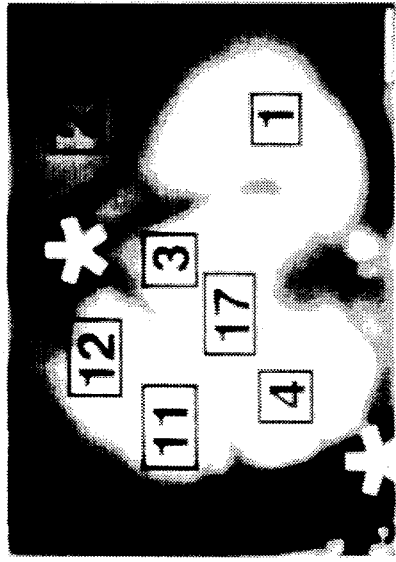
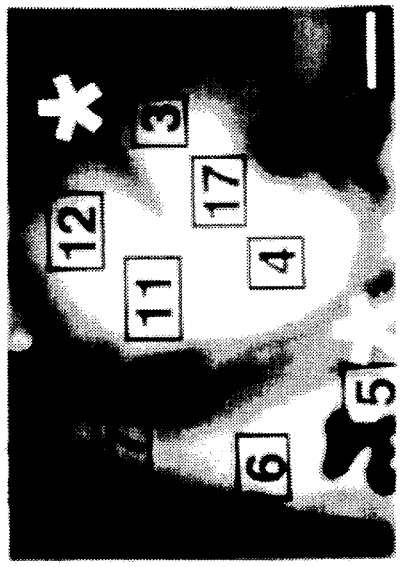

SOLID TUMOR, CORTICAL FUNCTION, AND NERVE TISSUE IMAGING METHODS AND DEVICE

CROSS-REFERENCE TO RELATED APPLICATIONS

This application is a continuation-in-part of U.S. patent application Ser. No. 07/894,270, filed Jun. 8, 1992, which is a continuation-in-part of U.S. patent application Ser. No. 07/565,454, filed Aug. 10, 1990, now U.S. Pat. No. 5,215,095.

TECHNICAL FIELD OF THE INVENTION

The present invention provides a method for real-time detection of solid tumor tissue, plus an ability to grade and characterize tumor tissue. The present invention further provides a method for real-time mapping of functional and dysfunctional cerebral cortex and nervous tissue. The present invention further provides a device for real-time detection and optical imaging for the inventive methods.

BACKGROUND OF THE INVENTION

A primary goal of neurological surgery is the complete removal of abnormal or pathological tissue while sparing normal areas. Hence, the neurosurgeon attempts to identify boundaries of pathological or dysfunctional tissue and to map adjacent areas of the cortex committed to important functions, such as language, motor and sensory areas so that pathological/dysfunctional tissue is removed without removing functional areas.

Incidence rates for primary intracranial brain tumors are in the range of 50–150 cases per million population or about 18,000 cases per year (Berens et al. 1990). Approximately one half of brain tumors are malignant. The incidence of malignant brain tumors in adults is predominantly in the age range of 40–55 years while the incidence of more benign tumors peaks near 35 years of age. A primary means for treatment of such tumors is surgical removal. Many studies have shown that when more of the total amount of tumor tissue is removed, the better the clinical outcome. For gross total resections of tumors, the 5-year survival rate is doubled when compared to subtotal resection. Both duration of survival and independent status of the patient are prolonged when the extent of resection is maximized in malignant gliomas. Current intraoperative techniques do not provide rapid differentiation of tumor tissue from normal brain tissue, especially once the resection of the tumor begins. Development of techniques that enhance the ability to identify tumor tissue intraoperatively may result in maximizing the degree of tumor resection and prolonging survival.

Of the 500,000 patients projected to die of systemic cancer per year in the United States, approximately 25%, or over 125,000 can be expected to have intracranial metastasis. The primary focus for surgery in this group is in those patients with single lesions who do not have widespread or progressive cancer. This group represents about 20–25% of patients with metastases (30,000), however, the actual number of patients that are good candidates for surgery is slightly smaller. Of those patients undergoing surgery, one half will have local recurrence of their tumor at the site of operation, while the other half will develop a tumor elsewhere. The fact that about 50% of the surgeries fail at the site of operation means that an improved ability to remove as much tumor as possible by detecting and localizing tumor margins during tumor removal could potentially decrease the incidence of local recurrence.

Thus, for both primary and metastatic tumors, the more tumor tissue removed, the better the outcome and the longer the survival. Further, by maximizing the extent of resection, the length of functional, good quality survival is also increased.

Most current tumor imaging techniques are performed before surgery to provide information about tumor location. Presurgery imaging methods include magnetic resonance imaging (MRI) and computerized tomography (CT). In the operating room, only intraoperative ultrasound and stereotaxic systems can provide information about the location of tumors. Ultrasound shows location of the tumor from the surface but does not provide information to the surgeon once surgery begins to prevent destruction of important functional tissue while permitting maximal removal of tumor tissue. Stereotaxic systems coupled with advanced imaging techniques have (at select few hospitals) been able to localize tumor margins based upon the preoperative CT or MRI scans. However studies (Kelly, 1990) have shown that the actual tumor extends 2–3 cm beyond where the image enhanced putative tumor is located on preoperative images. Therefore, the only current reliable method to determine the location of tumors is by sending biopsies during surgery (i.e., multiple histological margin sampling) and waiting for results of microscopic examination of frozen sections. Not only is it not advisable to continually take breaks during surgery, but such biopsies are, at best, an estimation technique and are subject to sampling errors and incorrect readings as compared to permanent tissue sections that are available about one week later. Thus, a surgeon often relies upon an estimation technique as a guide when patient outcome is dependent upon aggressive removal of tumor tissue. Surgeons have difficult decisions between aggressively removing tissue and destroying surrounding functional tissue and may not know the real outcome of their procedure until one week later and this may require an additional surgical procedure.

Multiple histological margin sampling suffers several drawbacks. First this is a time-consuming procedure as it can add about 30 to 90 minutes (depending upon the number of samples taken) to a surgical procedure when the patient is under anesthesia. Second, this procedure is prone to errors as a pathologist must prepare and evaluate samples in short order. Third, it is certainly the case that margin sampling does not truly evaluate all regions surrounding a primary tumor as some areas of residual tumor can be missed due to sampling error. Fourth, increased time for margin sampling is expensive as operating room time costs are high and this leads to increased overall medical costs. Moreover, increased operating room time for the patient increases the probability of infection.

Other techniques developed to improve visual imaging of solid tumor masses during surgery include determining the shape of visible luminescence spectra from normal and cancerous tissue. According to US Patent 4,930,516, in cancerous tissue there is a shift to blue with different luminescent intensity peaks as compared to normal tissue. This method involves exciting tissue with a beam of ultraviolet (UV) light and comparing visible native luminescence emitted from the tissue with a historical control from the same tissue type. Such a procedure is fraught with difficulties because a real time, spatial map of the tumor location is not provided for the use of a surgeon. Moreover, the use of UV light for an excitation wavelength can cause photodynamic changes to normal cells, is dangerous for use in an operating room, and penetrates only superficially into tissue and requires quartz optical components instead of glass.

Therefore, there is a need in the art for a more comprehensive and faster technique and a device for assisting such a technique to localize for solid tumor locations and map precise tumor margins in a real-time mode during surgery. Such a device and method should be further useful for inexpensive evaluation of any solid tumor (e.g., breast mammography) by a noninvasive procedure and capable of grading and characterizing the tumors.

There is also a need to image brain functioning during neurosurgical procedures. For example, a type of neurosurgical procedure which also exemplifies these principles is the surgical treatment of intractable epilepsy (that is, epilepsy which cannot be controlled with medications). Presently, electroencephalography (EEG) and electrocorticography (ECoG) techniques are used prior to and during surgery for the purposes of identifying areas of abnormal brain activity, such as epileptic foci. These measurements provide a direct measurement of the brain's electrical activity.

Intraoperative EEG techniques involve placing an array of electrodes upon the surface of the cortex. This is done in an attempt to localize abnormal cortical activity of epileptic seizure discharge. Although EEG techniques are of widespread use, hazards and limitations are associated with these techniques. The size of the electrode surface and the distance between electrodes in an EEG array are large with respect to the size of brain cells (e.g., neurons) with epileptic foci. Thus, current techniques provide poor spatial resolution (approximately 1.0 cm) of the areas of abnormal conical activity. Further, EEG techniques do not provide a map of normal conical function in response to external stimuli (such as being able to identify a cortical area dedicated to speech, motor or sensory functions by recording electrical activity while the patient speaks). A modification of this technique, called conical evoked potentials, can provide some functional cortical mapping. However, the cortical evoked potential technique suffers from the same spatial resolution problems as the EEG technique.

The most common method of intraoperative localization of cortical function in epilepsy and tumor surgery is direct electrical stimulation of the cortical surface with a stimulating electrode. Using this technique, the surgeon attempts to evoke either an observed motor response from specific parts of the body, or in the case of an awake patient, to generate specific sensations or cause an interruption in the patient's speech output. Again, this technique suffers from the same problems as the EEG technique because it offers only crude spatial localization of function.

Possible consequences of the inaccuracies of all these techniques, when employed for identifying the portion of the cortex responsible for epileptic seizures in a patient, are either a greater than necessary amount of conical tissue is removed possibly leaving the patient with a deficit in function, or that not enough tissue is removed leaving the patient uncured by the surgery. Despite these inadequacies, such techniques have been deemed acceptable treatment for intractable epilepsy. The same principles apply to tumor surgeries, however, intraoperative functional mapping is not performed routinely.

In the past few years, researchers have been using imaging techniques in animal models to identify functional areas of cortex with high spatial resolution. One type of such technique uses a voltage-sensitive dye. A voltage-sensitive dye is one whose optical properties change during changes in electrical activity of neuronal cells. The spatial resolution achieved by these techniques is near the single cell level. Blasdel and Salama (*Nature* 321:579, 1986) used a voltage-sensitive dye (merocyanine oxazolone) to map cortical function in a monkey model. The use of these kinds of dyes would pose too great a risk for use in humans in view of their toxicity. Further, such dyes are bleached by light and must be infused frequently.

Recently, measurement of intrinsic signals have been shown to provide similar spatial resolution as voltage-sensitive dye imaging. Intrinsic signals are light reflecting changes in cortical tissue partially caused by changes in neuronal activity. Unlike other techniques used for imaging neuronal activity, imaging intrinsic signals does not require using dyes (which are often too toxic for clinical use) or radioactive labels. For example, Grinvald et al. (*Nature* 324:361, 1986) measured intrinsic changes in optical properties of conical tissue by reflection measurements of tissue in response to electrical or metabolic activity. Light of wavelength 500 to 700 nm may also be reflected differently between active and quiescent tissue due, to increased blood flow into regions of higher neuronal activity. Another aspect which may contribute to intrinsic signals is a change in the ratio of oxyhemoglobin to deoxyhemoglobin.

Ts'o et al. (*Science* 249:417, 1990)used a charge-coupled device (CCD) camera to detect intrinsic signals in a monkey model. However, this technique would not be practical in a clinical environment because imaging was achieved by implanting a stainless steel optical chamber in the skull and in order to achieve sufficient signal to noise ratios, Ts'o et al. had to average images over periods of time greater than 30 minutes per image. By comparison to all other known techniques for localizing cortical function, imaging intrinsic signals is a relatively non-invasive technique.

Mechanisms responsible for intrinsic signals are not well understood, possible sources of intrinsic signals include dilatation of small blood vessels, increased scattering of light from neuronal activity-dependent release of potassium, or from swelling of neurons and/or glial cells.

Therefore, there is a need in the art for a procedure and apparatus for real-time optical imaging of cortical tissue which can precisely and quickly distinguish normal and abnormal cortical tissue. There is also a need in the art for developing a method that can image intrinsic signals with high spatial resolution, provide immediate images and be compatible with normal procedures in the operating room. This invention was made, in part, in an effort to satisfy this need.

SUMMARY OF THE INVENTION

The inventive method and device can be used to identify, grade and characterize solid tumors by imaging changes in electromagnetic absorption which reflects dynamics of dye perfusion through tissue, wherein the inventive device is able to differentiate tumor tissue from surrounding normal tissue with dynamic changes in optical signals during dye perfusion. Further, the inventive method and device can be used to identify areas of neuronal activity during neurosurgical procedures. In particular, this invention can be used by a neurosurgeon intraoperatively to identify areas in the brain dedicated to important functions such as vision, movement, sensation, memory and language. Further the present inventive method and device can be used to detect areas of abnormal cortical activity, such as epileptic foci. Lastly, the present invention can be used to identify individual nerves during neurosurgical procedures for tumor removal or anastamoses of severed nerves.

The present invention provides an apparatus for imaging tumor tissue or for real-time surgical imaging of cortical intrinsic signals or visualizing margins of solid tumor tissue from dynamic changes in optical signals during dye perfusion, comprising, a means for obtaining a series of analog video signals, and a means for processing the analog video signals into either an averaged control image or a subsequent averaged image, a means for acquiring and analyzing a plurality of subsequent images and averaged control images to provide a difference image, wherein the difference image is processed to account for movement and noise and to amplify the changes across a dynamic range of the apparatus, and a means for displaying the difference image alone or superimposed over an analog video image.

The present invention further provides a method for imaging tumor margins and dimensions of solid tumor tissue located in an area of interest, comprising illuminating the area of interest with spatially even, intensive and non fluctuating light containing a wavelength of electromagnetic radiation (emr) (e.g., light) absorbed by a dye, obtaining a video signal of the area of interest as a series of frames and processing the series of frames into an averaged control image, administering the dye by bolus injection into vasculature circulating to the area of interest, obtaining a subsequent series of frames of the area of interest over time and processing the subsequent series of frames into a subsequent averaged image, comparing each subsequent averaged image with the averaged control image to obtain a series of difference images, and comparing each difference image for initial evidence of changed optical signals within the area of interest which is the outline of solid tumor tissue, wherein tumor tissue is characterized by different kinetics of dye uptake compared to normal tissue and a temporally changed pattern of altered absorption of light as a result of increased vascularity of solid tumor tissue. Examples of appropriate dyes include indocyanine, fluorescein, hematoporphyrin, and fluoresdamine. A preferred dye is indocyanine green which has a broad absorption wavelength range and a peak absorption in the range of 730 nm to 840 nm.

The present invention further comprises a method in real-time for optically imaging functional areas of interest of the cortex in a patient comprising illuminating the area of interest with high intensity emr containing near-infrared wavelengths of emr, obtaining a series of frames of the area of interest and processing the series of frames into an averaged control image, administering a stimulus paradigm to the patient to stimulate an intrinsic signal, obtaining a series of subsequent frames of the area of interest over time and processing the subsequent series of frames into a subsequent averaged image, comparing each subsequent averaged image with the averaged control image to obtain a series of difference images, and comparing each difference image for initial evidence of an intrinsic signal within the area of interest, whereby an intrinsic signal is characterized by a change in emr reflectance properties manifest as a signal in the difference image.

The present invention further includes a method for imaging damage to a peripheral or cranial nerves comprising: (a) illuminating an area of interest with high intensity emr, wherein the area of interest comprises the peripheral nerve of interest including the suspected site of damage and a region adjacent of the suspected site of damage; (b) obtaining a series of frames of the area of interest and processing the series of frames into an averaged control image; (c) stimulating the peripheral or cranial nerve at a site adjacent of the suspected damaged site; (d) obtaining a series of subsequent frames at the time of stimulation and processing the series of subsequent frames into a subsequent averaged image; and (e) obtaining a difference image by subtracting the averaged control image from the subsequent averaged image to visualize the active region of the peripheral or cranial nerve, whereby nerve blockage is visualized as the point along the nerve where the intrinsic signal from the stimulated nerve abruptly ends, or is altered, attenuated or diminished in the difference image.

The present invention further includes a method for imaging tumor tissue surrounding or adjacent to nerve tissue to aid in selective resection of tumor tissue without destroying nerve tissue, comprising: (a) illuminating an area of interest with high intensity emr containing wavelength of emr absorbed by a dye; (b) obtaining a series of frames of the area of interest and processing the series of flames into an averaged control image; (c) stimulating the nerve; (d) obtaining a series of subsequent nerve frames and processing the subsequent series of nerve flames into a subsequent nerve averaged image; (e) obtaining a nerve difference image by subtracting the nerve averaged control image from the nerve subsequent averaged image to visualize the active nerve; (f) administering a dye into an artery feeding the area of interest; (g) obtaining a series of tumor subsequent frames and processing the tumor subsequent series of frames into a tumor subsequent averaged image; and (h) obtaining a tumor difference image by subtracting the tumor averaged control image from the tumor subsequent averaged image to create a tumor difference image that is capable of visualizing the tumor. Further, the tumor difference image and the nerve difference image can be superimposed upon each other to simultaneously visualize the relative locations of tumor tissue and nervous tissue.

The present invention further comprises a method for enhancing sensitivity and contrast of the images obtained from tumor tissue or intrinsic signal difference images, comprising: (a) illuminating an area of interest with a plurality of wavelengths of emr, wherein there is at least a first wavelength of emr and a second wavelength of emr; (b) obtaining a sequence of frames corresponding to each wavelength of emr, wherein a first sequence of frames is from the first wavelength of emr, the second sequence of frames is from the second wavelength of emr and so on; (c) processing the first sequence of frames into a first averaged control image, the second sequence of frames into a second averaged control image and so on; (d) stimulating for intrinsic signals or administering a dye for tumor tissue imaging; (e) obtaining a first series of subsequent frames using the first wavelength of emr, a second series of subsequent frames using the second wavelength of emr, and so on, and processing the first, second and so on subsequent series of frames into the first, second and so on subsequent averaged images, respectively; (f) obtaining a first difference image by subtracting the first averaged control image from the first subsequent averaged image and a second difference image by subtracting the second averaged control image from the second subsequent averaged image, and so on; and (g) obtaining an enhanced difference image by ratioing the first difference image to the second difference image. Preferably, the monochromatic emr sources to illuminate the area of interest are from laser sources. This technique is useful for obtaining three dimensional information of the area of interest.

BRIEF DESCRIPTION OF THE DRAWINGS

FIG. 1 (A, B, C, and D) illustrates a view of human cortex just anterior to face-motor cortex with one recording (R) and two stimulating electrodes (s), and three sites (#1, #2, #3) where average percent changes were determined. Averages of 128 images (4/sec) were acquired at 30 Hz and stored (1/sec). Alter acquiring 3-6 averaged control images (5 sec/image), a bipolar cortical stimulation evoked epileptiform afterdischarge activity.

FIG. 2 illustrates a spatial map of stimulation induced epileptiform activity. This Figure shows a comparison between different degrees of activation for both spatial extent and amplitude of optical change graded with the extent of cortical activity. Specifically, FIG. 2 shows percentage difference images from various times during two stimulation trials from those described in FIG. 1. The top 3 pictures (2A2, 2B2, and 2C2) are from stimulation trial 2 where 6 mA cortical stimulation evoked a brief period of afterdischarge. These are compared to the bottom three pictures (A4, B4, and C4) which are from stimulation trial 4 showing the optical changes evoked by cortical stimulation at 8 mA. FIGS. 2, 2A2 and 2A4 compare control images during rest. FIGS. 2, B2 and B4 compares the peak optical changes occurring during the epileptiform afterdischarge activity. FIGS. 2, 2C2 and 2C4 compares the degree of recovery 20 seconds after the peak optical changes were observed. The magnitude of optical change is indicated by the gray-scale changes. Each image maps an area of cortex approximately 4 cm by 4 cm.

FIG. 3 shows a sequence of dynamic changes of optical signals identifying active areas and seizure foci. This Figure shows eight percentage difference images from the stimulation trial 2 described in the previous two Figures. Each image is integrated over a two second interval. The focal area of greatest optical change is in the center of images 3C, 3D, and 3E, indicating the region of greatest cortical activity. This region is the epileptic focus. The magnitude of optical change is indicated by the gray-scale bar on the right side of the Figure. The arrow beside this gray-scale indicates the direction of increasing amplitude. Each image maps an area of cortex approximately 4 cm by 4 cm.

FIG. 4 illustrates a real-time sequence of dynamic changes of stimulation-evoked optical changes in human cortex. FIG. 4, panels 4A–4H, show eight consecutive percentage difference images, each image is an average of 8 frames ( <¼ second per image). The magnitude of optical change is indicated by the gray-scale 4A–4H changes. Each image maps to an area of cortex that is approximately 4 cm by 4 cm. This Figure demonstrates that the inventive device and method can be used to map, in real time, dynamics of optical changes and present such information to the surgeon in an informative format.

FIG. 5 shows an activation of somatosensory cortex by stimulation of a peripheral nerve in an anesthetized rat (afferent sensory input by directly stimulating the sciatic nerve in the hind limb of a rat). The leftmost image 5A is a gray-scale image of hind limb somatosensory cortex in an anesthetized rat. The magnification is sufficiently high so that individual capillaries can be distinguished (the smallest vessels visible in this image). The center image 5B is an image of a percentage difference control optical image during rest. The magnitude of optical change is indicated by the gray-scale bar in the center of this image. The rightmost image 5C is a percentage difference map of the optical changes in the hind limb somatosensory cortex during stimulation of the sciatic nerve.

FIG. 6 shows functional mapping of human language (Broca's area) and tongue and palate sensory areas in an awake human patient. During three "tongue wiggling" trials images were averaged (32 frames, 1 sec) and stored every 2 seconds. A tongue wiggling trial consisted of acquiring 5–6 images during rest, then acquiring images during the 40 seconds that the patient was required to wiggle his tongue against the roof of his mouth, and then to continue acquiring images during a recovery period. The same patient engaged in a "language naming" trial. A language naming trial consisted of acquiring 5–8 images during rest (control images—the patient silently viewing a series of blank slides), then acquiring images during the period of time that the patient engaged in a naming paradigm (naming a series of objects presented with a slide projector every 2 seconds, selected to evoke a large response in Broca's area), and finally a series of images during a recovery period following a time when the patient cease his naming task (again viewing blank slides while remaining silent). Images A1 and B1 6A1 and 6B1 are gray-scale images of an area of human cortex with left being anterior, right-posterior, top-superior, and the Sylvan fissure on the bottom. The two asterisks on 6A1, 6B1, 6A2, and 6B2 serve as reference points between these images. The scale bars in the lower right corner of 6A1 and 6B1 are equal to 1 cm. In 6A1, the numbered boxes represent sites where cortical stimulation with electrical stimulating electrodes evoked palate tingling (1), tongue tingling (2), speech arrest-Broca's areas (3,4) and no response (11, 12, 17, 5-premotor). Image 6A2 is a percentage difference control image of the cortex during rest in one of the tongue wiggling trials. The gray-scale bar on the right of 6A2 shows the relative magnitude of the color code associated with images 6A2, 6A3, 6B2 and 6B3. Image 6A3 is a percentage difference map of the peak optical changes occurring during one of the tongue wiggling trials. Areas identified as tongue and palate sensory areas by cortical stimulation showed a large positive change. Suppression of baseline noise in surrounding areas indicated that, during the tongue wiggling trials, language-motor areas showed a negative-going optical signal. Image 6B2 is percentage difference control image of the cortex during one of the language naming trials. Image 6B3 is a percentage difference image of the peak optical change in the cortex during the language naming task. Large positive-going signals are present in Broca's area. Negative-going signals are present in tongue and palate sensory areas.

FIG. 7 shows a time course and magnitude plot of dynamic optical changes in human cortex evoked in tongue and palate sensory areas and in Broca's area (language). This Figure shows the plots of the percentage change in the optical absorption of the tissue within the boxed regions shown in FIG. 6, images 6A1 and 6B 1, during each of the three tongue wiggling trials and one of the language naming trials (see, description of FIG. 6).

FIG. 9 illustrates a timecourse and magnitude of dynamic optical changes in human cortex evoked in Wernicke's area (language comprehension).

FIG. 10 illustrates differential dynamics of dye to identify low grade human CNS tumor. This series of images are from a patient having a low grade CNS tumor (astrocytoma, grade 1 ). FIG. 10D top right) shows that in this low grade tumor, all tissue (both normal and abnormal) showed staining at 45 sec after dye administration. FIG. 10E middle right) is one minute after dye administration and FIG. 10F is five minutes after dye administration (showing complete clearance in this low grade tumor). These data show that indocyanine green enters low grade tumor tissue faster than normal brain tissue, and may take longer to be cleared from benign tumor tissue than normal tissue, providing utility to image even low grade tumors, and to distinguish intraoperatively, low grade tumor tissue from surrounding normal tissue.

FIG. 13 shows that differential dynamics of dye can identify and characterize tumors in human patients that do not contrast enhance with MRI imaging. A proportion of non-benign tumors are not observable with present MRI imaging techniques. The images in this Figure are from a patient whose tumor did not contrast enhance with MRI. This lack of enhancement is usually typical of benign tumors. However, optical imaging was able to identify this tumor as a non-benign type (an anoplastic astrocytoma as shown one week later by pathology and flow cytometry). As shown in FIGS. 10, 11, and 12, this dynamic trait is a characteristic of a non-benign tumor.

FIG. 11C shows that 5 seconds after dye injection the dye can be seen to profuse through both normal and tumor tissue.

FIG. 16 shows a spatial map of dynamic changes in tumor vs. non-tumor areas in the rat glioma model. The sequence of images in this figure demonstrate the dynamic differences of the absorption changes due to dye between tumor and non-tumor tissue.

FIG. 18 shows dynamic imaging of dye uptake reveals residual traces of tumor cells in resected tumor margins. This is a continuation of the study on the same animal shown in FIGS. 14 through 17.

DETAILED DESCRIPTION OF THE INVENTION

Figure 1A:
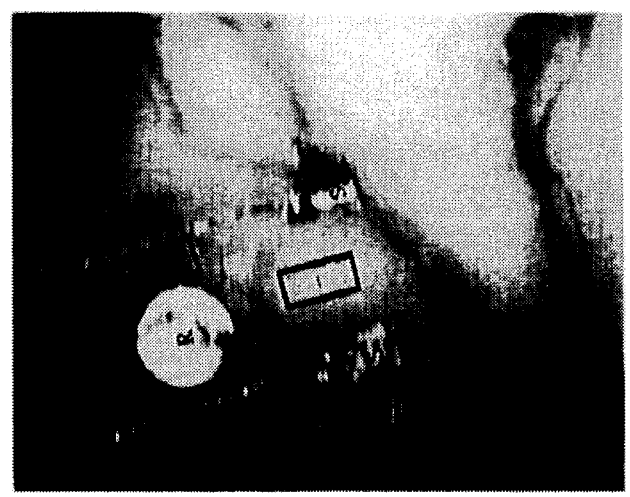
FIG. 1A is a view of a human cortex just anterior to face-motor cortex with one recording electrode (R) and two stimulating electrodes (s), and four sites (the boxed areas labeled 1, 2, 3, and 4 ) where the average percent changes of absorption over these areas were determined. The cortex was illuminated with emr >690 nm.

The present invention provides an apparatus for imaging neuronal intrinsic signals in real time and for determining the presence, size, margins, dimensions, and grade of a solid tumor mass using a dye. The present invention further provides a method for functional mapping of the cortex in a patient by mapping intrinsic signals in real time, a method for determining the presence, size, location, and grade of solid tumor tissue in real time without the sampling errors of biopsies or the delay of and possible misdiagnosis of the pathologist's frozen section analysis, and a method for imaging nerve tissue that may be physically damaged or surrounded by and adjacent to tumor cells. The inventive methods employ a similar apparatus, comprising a series of components, including video input hardware and dedicated image processing hardware. The video input hardware is, for example, a photo-detector, such as a CCD (charge coupled device) camera (preferably a COHU 6510 CCD Monochrome Camera with a COHU 6500 electronic control box made by COHU Electronics San Diego, Calif.). In some cameras the analog signal is digitized 8-bits deep on an ADI board (analog-to-digital board). The dedicated image processing hardware is generally controlled by a "host computer". The host computer is any common general computer (such as an IBM PC type with an Intel 386, 486 or better microprocessor or Sun SPAR. C) that is interfaced with the dedicated imaging hardware and sends commands to the imaging hardware that direct data flow, computations, image acquisition and the like. Thus, the host computer directs the actions of the imaging hardware and provides the user interface.

Definitions

The following are definitions of commonly used terms and that are applied in this application according to their an-accepted usage, such as described in Inoue, *Video Microscopy* Plenum Press, New York, 1989.

Area of Interest is that area of tissue that comprises the subject of the image.

Arithmetic Logic Unit (ALU) is the hardware component that performs a variety of mathematical and logic operations (e.g., sum, difference, exclusive or, multiply by a constant, etc.) on the image signal at extremely high speeds.

Averaged Control Image is that updateable image that is the average of a series of real time images over a period of time.

Charge Coupled Device (CCD) is a photo-sensitive silicon chip used in place of a pickup tube in miniature video cameras.

Difference Image is the manipulated image created by adding or subtracting a subsequent image or a particular image in time from an averaged control image.

Frame is a single digitized array of single video pictures.

Frame Buffer is a piece of hardware that serves as a temporary storage of a frame, such as an averaged control image, a subsequent image or a difference image.

Geometric Transformation (Gonzalez and Wintz, *Digital Image Processing,* Addison-Wesley Publishing Co., Reading, 1987) generally modify spatial relationships between pixels in an image. For this reason, geometric transformations are often called "rubber sheet transformations" because they can be viewed as the process of "printing" an image on a sheet of rubber and stretching this sheet according to a predefined set of rules. As applied to video imaging, subsequent images can be viewed as having been distorted due to movement and it is desirable to "warp" these images so that they are similar to the control images. Geometric transformations are distinguished from "point transformations" in that point transformations modify a pixel's value in an image based solely upon that pixel's value and/or location and no other pixel values are involved in the transformation.

Image is a frame or composition of frames that have been altered after digitization, such as processing a sequence of frames into an averaged control image or a subsequent averaged image.

Intrinsic Signal means a detectable change in reflectance properties of neuronal tissue due to endogenous physiologic activity. Possible causes of intrinsic signals include, for example, membrane depolarization, glial cell swelling, ion flux across neuronal membranes, blood volume changes, blood deoxygenation (hemoglobin to deoxyhemoglobin), tissue oxygenation and combinations thereof.

Linear Histogram Stretch is a transformation in which the values between two points (high, low) are remapped to cover a full range of values (i.e., dynamic range). For example, the low value is mapped to zero, the high to 255, and the intermediate values are mapped to linearly increasing brightness values. All brightness values below the low value are set to zero and all brightness values above the high value are set to the high value.

Look Up Table (LUT) is a piece of hardware that functions to store memory that directs conversion of the gray value of each pixel into another gray value or color that is specified by the LUT. The LUT can be programmed to manipulate image contrast, threshold an image, apply pseudocolor and the like (such as a convenient implementation method for point processing algorithms). In the case of the present invention, the LUTs are, preferably, implemented for speed on an ADI and/or ALU boards.

Paradigms cause a change in electrical activity of an area of cortical tissue dedicated to a specific function (e.g., speech, language, vision, etc.) thus causing an increase or decrease in what is called an intrinsic signal.

Pixel is the individual units of image in each frame of the digitized signal. The intensity of each pixel is linearly proportional to the intensity of illumination before signal manipulation and corresponds to the amount of emr (photons) being reflected from a particular area of tissue corresponding to a particular pixel. It should be noted that an image pixel is the smallest unit of a digital image and its output intensity can be any value. A CCD pixel is the smallest detecting element on a CCD chip and its analog output is linearly proportional to the number of photons it has detected.

Processed Difference Image is the raw difference image that has been processed or manipulated to filter out noise or movement and increase the dynamics of effect of different pixel values to illustrate events in the area of interest.

Tumor Margin is the area where the surgeon has resected the tumor.

Apparatus

The inventive apparatus is made as one unit or a group of components. The first component is a high intensity emr source. The emr source is for illuminating the cortical surface or area of interest, such as an area suspected of having solid tumor tissue. Different intrinsic signals can be illuminated by different wavelengths of emr. Moreover, the emr source must include the wavelengths of emr absorbed by the dye for the tumor imaging method. For example, when the dye is indocyanine green, preferred wavelengths are from about 730 nm to about 840 nm. For other dyes, the preferred wavelengths of illuminating emr should include wavelengths at which the dye absorbs. The term emr instead of light is used because it is also possible to image in the infrared region of the spectrum outside of the visible light range.

When determining intrinsic signals from the cortex, reflected emr can be filtered to allow for video imaging of only selected wavelengths of emr. Preferred selected wavelengths of emr include, for example, from about 500 nm to about 900 nm, or most preferably, the near infrared spectrum. Generally, longer wavelengths (e.g., approximately 800 nm) measure deeper cortical activity.

Moreover, that pan of the infrared spectrum in an invisible range of between 0.75 to about 1000 micrometers allows for a determination of intrinsic signals through dura and skull, thereby allowing for a determination of intrinsic signals through intact skull and dura and without the risks associated with neurosurgery. When using this range of far infrared wavelengths, an IR detector is a different device than a CCD chip for a visible analog camera. IR detectors are made from materials such as indium arsenide, germanium and mercury cadmium telluride rather than silicon. IR detectors must be cryogenically cooled in order that they be sensitive to small changes in temperature. For example, one IR imaging system is an IRC-64 infrared camera (Cincinnati Electronics, Mason, Ohio).

As heat reaches the surface of the cortex, it emits electromagnetic radiation in the range of about 3-5 or 8-14 microns. Others have attempted to image this emitted radiation (see, for example, Gorbach et al., "Infrared Mapping of the Cerebral Cortex" *Thermography* 3:108, 1989). However, according to the present invention these emitted wavelengths are filtered out and an IR detector instead of a CCD detector is used. An IR emr source is, for example, a Tunable IR Diode Laser from Laser Photonics, Orlando, Fla. The imaged wavelengths are different from body heat and images of changes in absorption and emr scattering can be obtained according to the inventive method. In the case of tumor images through intact skin and possibly bone, a dye that absorbs in the IR can be used (e.g., indocyanine green). Other useful dyes include, for example, Photofrin® derived from a hematoporphyrin derivative (HPD) and absorbs light at 630 nm, mono espatyl chlorin-36 (NPe$_6$, Nippon Petrochemical, Japan), benzoporphyrin derivative (BPD, Quadra Logic Vancouver BC), Evans Blue, and combinations thereof.

Preferably, the emr source is a high intensity, broad spectrum emr source, such as a tungsten-halogen lamp and a cutoff filter for all wavelengths below 695 nm. Most preferably, the emr source is directed to the area of interest by a fiber optic means. An example of such a emr source is a fiber optic emr passing through a beam splitter, controlled by a D.C. regulated power supply (Lambda, Inc.) and passed through a 695 nm longpass filter.

The inventive apparatus includes a means for obtaining an analog video signal of the cortex or area of interest. A preferred device for obtaining an analog video signal is a charge coupled device (CCD) video camera which creates an output video signal at 30 Hz having, for example, 512 horizontal lines per frame using standard RS 170 convention. One such device is a CCD-72 Solid State Camera (Dage-MTI Inc., Michigan City, Ind.) and another such device is a COHU 6500 (COHU, San Diego, Calif.).

The area of interest must be evenly illuminated to better adjust the signal over a full dynamic range. If there is uneven illumination in the area of interest, it will limit the dynamic range. Preferably a high intensity and diffuse or even lighting system is used. Techniques to obtain even illumination over the area of interest include, for example, diffuse lighting, image processing algorithms to compensate for uneven illumination on a digitized image, a constant shade gray image marker point in the area of interest as a control point, a wavelength cutoff filter in front of the camera and/or emr source, or combinations thereof. Preferably, a regulated power supply will prevent fluctuations in emr sources. A footplate system is an optical glass (sterile) contacting and covering the area of interest to provide a flatter contour. The footplate also retards tissue movement.

The analog signal must first be adjusted to maximize sensitivity of detection (at the level of the analog signal and before digitizing) to amplify the signal and spread the signal across the full possible dynamic range, thereby increasing sensitivity of the apparatus. 60 Hz noise (such as from A.C. power lines) is filtered out in the camera control box by an analog filter. Such adjustments further serve to enhance, amplify and condition the analog signal from the CCD. One means for properly adjusting the input analog signal is to digitize this signal at video speed (30 Hz), and view the area of interest as a digitized image that is converted back to analog.

It is important to compensate for small movements of tissue or the patient during the imaging process. Larger patient movements require a new orientation of the camera and obtaining a new averaged control image. Compensating for movement can be done by mechanical or computational means or both. Mechanical means include, for example, placing a footplate over the area of interest wherein the footplate comprises sterilized optical quality glass in a framing device, and/or securing the camera and possibly the emr source to the skeletal frame of the patient, and combinations of both. When the camera and/or emr source are attached to the skeletal structure of the patient, any patient movements will not effect the image because the camera and illumination source will remain in a constant orientation to the area of interest. The advantage of the footplate is that it retards tissue movement caused by arterial pressure and/or respiration and prevents changes due to evaporation of cerebrospinal fluid. Computational means include, for example, using functional control points in the area of interest and triangulation-type algorithms to compensate for movements of these control or tie points, and "image warping" techniques whereby each subsequent image is registered geometrically to the averaged control image to compensate for movement, and combinations of both techniques. The image warping technique is described in, for example, Wolberg, "Digital Image Warping" IEEE Computer Society Press, Los Alimitos, Calif. 1990. The image warping technique can further indicate when movement has become too great for the averaged control image and that a new averaged control image must be taken. Control points can be placed directly in the area of interest, such as directly on the cortical surface for intrinsic signal analysis. For example, Goshtasby ("Piecewise Linear Mapping Functions for Image Registration" in *Pattern Recognition* vol. 19 pp 459–66, 1986) describes a method whereby an image is divided into triangular regions using control points. A separate geometrical transformation is applied to each triangular region to spatially register each control point to a corresponding triangular region in a control image.

If the two images (averaged control image and subsequent image) are misaligned prior to subtraction, artifacts will result since the difference image will be more like a gradient image amplifying noise and edge information. Image misalignment can arise from patient motion, heartbeat and respiration. One solution is to fix the camera to a rigid assembly connected to the patient, such as his or her head such that any patient motion also moves the camera's field of view accordingly. Another solution is to perform real time motion compensation with motion detection and geometric transformation with the image processing board. Simple translation or more complicated (thus more accurate) unwarping can be implemented depending upon the input frame rate and amount of averaging.

In the case of imaging tissue (either for neuronal activity or for dynamical imaging of dye flow through tissue) in a human subject, it is necessary to compensate for the motion of the subject which may occur between the acquisition of consecutive images. For many types of images, it is possible to compensate by a geometrical compensation which transforms the image by translation in the x-y plane. In order for an algorithm such as this to be feasible, it must be computationally efficient (preferably implementable in integer arithmetic), memory efficient, and robust with respect to changes in ambient light.

One possible method would be to translate an image by 0 through k number of pixels in every possible direction with respect to the control image. For each of the $(2*k+1)*(2k+1)$ translations, make a subtraction image and calculate some metric to estimate the closeness to the control image. An example of such a metric would be the variance of the subtraction image. The drawback of this method is that it is not efficient since for each of $(2*k+1)*(2k+1)$ subtraction images, we would need to calculate the variance over $512 * 512$ pixels.

An efficient improvement of this algorithm is to estimate the variance of the subtraction images by randomly selecting some small number of areas of interest (for example, 9 areas of interest), each area consisting of a small number of pixels (say 8×8) from the image that one wishes to translate with respect to the control image. Also, choose some search depth (for example, 10 pixels) over which to translate these small areas of interest with respect to their corresponding areas of interest in the control image. After translation in all possible directions for 0 through 10 pixels, choose the translation which minimizes the variance over the selected areas of interest. Since all the areas of interest are the same size, division is not necessary in the calculation of the variance which is to be ordered so that the minimal variance can be selected. Hence, all calculations can be carried out in integer arithmetic. Since the areas of interest are sufficiently small, most of the data can be read into the host computer's RAM limiting IO to the frame buffers and increasing speed.

Another problem is guaranteeing uniformity in the illumination of the tissue surface. Nonuniformity comes from fluctuation in the illumination source and intensity variations resulting from the three-dimensional nature of the tissue surface. Fluctuation in the illumination source is addressed by using a light feedback mechanism to regulate the power supply of the illumination source. Both of these problems can also be compensated for in the image processing module.

The analog video signal is continuously fed into a means for processing the signal. One such means for acquiring and analyzing data is an image analyzer (e.g., Series 151 Image Processor, Imaging Technologies, Inc. Woburn, Mass.). An image analyzer can receive and digitize an analog video signal with an analog to digital interface and perform such a function at a frame speed of about 1/30th of a second (e.g., 30 Hz or "video speed"). Processing the signal involves first digitizing the signal into a series of pixels or small squares assigned a value (in a binary system) dependent upon the number of photons (i.e., quantity of emr) being reflected off tissue from the part of the area of interest assigned to that pixel. For example, in a standard 512×512 image from a current technology CCD, there would be 262,144 pixels per image. In an 8 bit system, each pixel is represented by 8 bits. One can cool the CCD to reduce thermal noise.

Preferably, the signal processing means includes a programmable look-up table (e.g., CM150-LUT16, Imaging Technology, Woburn, Mass.) initialized with values for convening gray coded pixel values, representative of a black and white image, to color coded values based upon the intensity of each gray coded value. This provides image enhancement via an image stretch. An image stretch is a technique whereby the highest and lowest pixel intensity values used to represent each of the pixels in a digital image frame are determined over a region of the image frame which is to be stretched. Stretching a selected region over a larger range of values permits, for example, easier identification and removal of relatively high, spurious values due to noise (e.g., glare).

Each image received is stored in the frame buffer, preferably within the context of a CPU as a frame of data elements represented, for example, as a 512 by 512 array of pixels. Each pixel has a 8 bit value corresponding to one of 256 levels of gray.

The processing means further includes a plurality of frame buffers having frame storage areas for storing frames of digitized image data received from the A/D interface. The frame storage area comprises at least one megabyte of memory space, and preferably at least 8 megabytes of storage space. An additional 16-bit frame storage area is preferred as an accumulator for storing processed image frames having pixel intensities represented by more than 8-bits. The frame butters are temporary fast memory. The processing means should include at least three frame buffers. One is for storing the averaged control image, another is for storing the subsequent image and a third is for storing a difference image between the averaged control image and the subsequent image.

The processing means further includes an arithmetic logic unit (ALU) (e.g., ALU-150 Pipeline Processor) for performing arithmetical (add, subtract, etc.) and logical (and, or, etc.) functions from data located in one or more frame buffers. An ALU is a fast processor. The ALU allows for image averaging in real time. For example, a newly incoming digitized image can be sent directly to the ALU and is added or subtracted to an averaged control image sitting in a frame buffer by passing both images through an ALU and adding them. After a last image is added, this 16 bit result can be sent again through an ALU which will divide this result by a constant (i.e., the total number of images). The output from the ALU is either stored in a frame buffer, sent for more processing, or used as its own input and again combined with another image.

It is important to compensate for patient movement in the digitized images before subtracting such images. Thus, geometric transformations are applied to the images so that they are geometrically registered prior to subtraction.

The inventive apparatus can enhance processing speed to create a difference frame by adding a real time modular processor or faster CPU chip to the image processor. For example, one real time modular processor is a 150 RTMP-150 Real Time Modular Processor (Imaging Technology, Woburn, Mass.).

The processing means further may include a means for performing a histogram stretch of the difference frames (e.g., Histogram/Feature Extractor HF 151-1-V module, Imaging Technology, Woburn, Mass.) to enhance each difference image across its dynamic range. A linear histogram stretch is described in, for example, Green, *Digital Image Processing: A Systems Approach,* Van Nostrand Reinhold, New York, 1983. A histogram stretch assigns the brightest pixel, or one with the highest value in the difference image and assigns this the maximum value. The smallest pixel value is assigned the minimum value and every other value in between is assigned a linear value (for a linear histogram stretch or a logarithmic value for a log histogram stretch, etc.) in between the maximum and minimum values. This allows the difference image to fully utilize the full dynamic range which provide for absolute changes.

The image processing system can use a variety of hardware that is available or under development. For example, the Texas Instrument Multimedia Video Processor (MVP) is under development for motion video applications. The MVP uses a highly parallel internal architecture, large on-chip memory, and extremely high bandwidth communication within CPU and between the CPU memory and I/O devices in order to provide in excess of 2 billion RISC-type operations per second performance necessary to support the requirement of real-time video compression standards and real-time image capture, processing and visualization. For example, the hardware can comprise of printed circuit board modules with interfaces to a VME bus. A single chassis can house all of the modules and reside on a rack that is easily transportable in an operating room or between operating rooms, along with display monitors and peripheral input and output devices. The real time system, for example, comprises four boards for acquisition image processing, peripheral control and host computer. A minimal configuration with reducing processing capabilities comprises just the acquisition and host computer boards. The acquisition board comprises circuitry to perform real-time averaging of incoming video frames and allow readout of averaged frames at a maximum rate bus. A VME bus is preferred because of its high peak bandwidth (greater than 80 Mbytes/sec for the latest revision, VME64) and compatibility with a multitude of existing VME products. The acquisition board must also support many different types of cameras via a variable scan interface. A daughter board can support the interfacing needs of many different types of cameras and supply variable scan signals to the acquisition motherboard. Preferably, the unit comprises a daughter board interfacing to an RS- 170A video signal to support a wide base of cameras. Other camera types, such as slow scan cameras with a higher spatial/contrast resolution and/or better signal to noise ratio) can be developed and incorporated into the inventive device, as well as improved daughter boards to accommodate such improved cameras.

The host computer comprises a single-board embedded computer with a VME interface. Preferably the host computer comprises a VME64 interface, or a standard (IEEE 1014-1987) VME interface, depending upon bus bandwidth considerations. Example of host computer boards include, for example, Force SPARC/CPU-2E and HP9000 Model 7471. The user interface can be, for example, a Unix/X-Widow environment. The image processing board can be, for example, based upon Texas Instruments' MVP and other chips to perform real time image averaging, registration and other processing necessary to produce high quality difference images for intraoperative viewing. This board will also drive a 120×1024 R6B display to show a sequence of difference images over time with pseudo-color mapping to highlight tumor tissue. Preferably, a second monitor is used for the host computer to increase the overall screen real estate and smooth the user interface. The processing board (fully programmable) can support a VME64 master interface to control data transactions with the other boards. Lastly, a peripheral control board can provide electrical interfaces to control mechanical interfaces from the host computer. Such mechanical interfaces can include, for example, a computer-controlled, motor-driven syringe for dye injection, light source, and camera control box.

The difference image signal is, preferably, further processed to smooth out the image and remove high frequency noise. For example, a lowpass spatial filter can block high spatial frequencies and/or low spatial frequencies to remove high frequency noises at either end of the dynamic range. This provides a smoothed-out processed difference image (in digital format). The digitally processed difference image can be color-coded by assigning a spectrum of colors to differing shades of gray. This image is then converted back to an analog image (by an ADI board) and displayed for a real time visualization of differences between an averaged control image and subsequent images. Moreover, the processed difference image can be superimposed over the analog image to display regions upon a video display of the area of interest, those specific tissue sites where the dye may have a faster uptake or where an intrinsic signal may be occurring.

The present invention further includes a means for subtractive processing of difference images to identify cortical areas of neuronal inhibition. Normally areas of increased neuronal activity result in an increase of the emr absorption capacity of neuronal tissue (i.e., the tissue gets darker if visible light is used for emr illumination, or an intrinsic signal increases in a positive direction). Similarly, a decrease in neuronal activity results in a decrease of emr absorption capacity of the tissue (i.e., the tissue appears brighter, or intrinsic signals become negative). For example, image A is a subsequent averaged image and image B is an averaged control image. Normally, when a pixel in image A is subtracted from a pixel in image B and a negative value results, this value is treated as zero. Hence, difference images cannot account for areas of inhibition. However, the present invention provides a method for identifying both negative and positive intrinsic signals, by the method comprising: (a) subtracting image A (a subsequent averaged image) from image B (an averaged control image) to create a first difference image, whereby all negative pixel values are zero; and (b) subtracting image B from image A to create a second difference image whereby all negative pixel values are zero; and adding the first and second difference images to create a "sum difference image". The sum difference image shows areas of increased activity (i.e., color coded with warmer colors such as yellow, orange, red) and show areas of less activity or inhibition (i.e., color coded with colder colors such as green, blue, purple). Alternatively, one can overlay the first difference image on the second difference image. Either method provides an image of increased neuronal activity and decreased neuronal activity.

Preferably, the processing means further includes an optical disk for storing digital image data, a printer for providing a hard copy of the digital and/or analog video image and a monitor to provide for the physician to continuously monitor the difference frame output (converted back to an analog signal) of the apparatus. The difference frame output may be superimposed upon the real time analog video image to provide a video image of the area of interest (e.g., conical surface or suspected tumor site) superimposed with a color-coded difference frame, in frozen time, to indicate where regions of faster dye uptake have occurred and where there are intrinsic signals in response to some stimulus or paradigm.

During a surgical procedure, there is often patient movement. In the case of an anesthetized patient, motion is often due to respiration and blood flow. In an awake patient, there will be additional movement. Movement must be compensated for in the digitized images so that the images are geometrically registered prior to subtraction. Geometric compensation is achieved by applying geometric transformations to the digitized images. One piece of image-processing hardware which can accomplish geometric transformations in real-time is a GP-150 Geometrical Processor board (Informatique et Techniques Avancees, Issy-les-Moulineaux, France). The GP-150 Processor board is compatible with Itex hardware and performs real time rotations, translations, zooms, and second degree distortion corrections at video rates with bilinear interpolation on 512×512×8-bit images.

Imaging Methods

The method for imaging a solid tumor involves periodically administering a dye by bolus injection into vasculature (e.g., artery or vein) perfusing the suspected tumor site in the area of interest. Preferably, the dye has a relatively short half life (e.g., less than five minutes) and is rapidly cleared to allow for repeated administration. The video CCD of the inventive apparatus is focused upon the suspected solid tumor site (area of interest) and high intensity emr containing the wavelength absorbed by the dye illuminates the site. Just prior to administration of the dye, the first averaged image is taken, digitized and stored in a frame buffer. The dye is injected quickly and rapidly as a bolus. Subsequent image frames are taken and stored and subtractively compared to produce difference images (e.g., one or two per second) using the inventive processing means. Initial visualization of the dye will appear in the difference image first in tumor tissue because the dye perfuses more rapidly into tumor tissue. Solid tumor margins will be the first images to appear in the difference frame as darkened lines outlining a solid tumor mass. This difference frame can be frozen and stored to allow the surgeon to study the tumor image and identify tumor margins in real time during an operation. Moreover, the dye will remain for a longer period of time in tumor tissue compared to normal tissue. Therefore, after there is general appearance of the dye throughout the area of interest in both normal tissue and tumor tissue, the dye clearance in tumor tissue will be delayed, allowing another opportunity to visualize tumor margins by dye presence in tumor tissue but not in normal tissue. In more aggressive or malignant tumors, the higher the tumor grade, the longer the dye remains in tumor tissue. For lower grade or more benign tumors, the dye remains in tumor tissue for 45 sec to 2 min, whereas the dye can remain in more malignant tumors for up to 10 minutes.

The inventive method is superior to established tumor imaging techniques, such as MRI (magnetic resonance imaging) because optical imaging can distinguish low grade tumors that cannot be distinguished with current MRI techniques (MRI is not an intraoperative technique) and updated images are continually available during a surgical procedure by readministering the dye. The dye can be administered on multiple occasions during a surgical procedure after resection has begun to look at resected walls for residual tumor tissue. For CNS tumors, MRI techniques require an advanced stage tumor that has compromised the blood brain barrier to be able to image such a tumor. The present optical imaging method, by contrast, can image even low grade tumors that have not yet compromised the blood brain barrier. Therefore, optical imaging is a more sensitive technique than MRI, can be used intraoperatively, and provides an approximate means for grading tumors.

The dye can be any emr-absorbing dye that is safe for in vivo administration, and has a short half-life when administered intravenously or intraarterially. Example of such a dyes are indocyanine green, Photofrin®, $NPe_6$, BPD, Evans Blue, and combinations thereof. Further, during surgical resection of a solid tumor, it is important that the dye be rapidly cleared from the area of interest. In that way, there can be repeated dye administrations to determine residual tumor tissue during resection.

During an imaging study, it is important to continually update the averaged image frame to account for patient movement, particularly for an awake patient. This will account for circulating residual dye and patient movements or tissue movements due to surgical manipulation.

For example, the inventive method for visualizing tumor tissue was utilized in a rat glioma model of the frontal lobe to test the ability of the inventive method to identify normal or edematous brain from tumor tissue and to determine if the inventive method could separate normal from abnormal tissue after all visible tumor had been resected. The dynamic nature of the dye's perfusion through the brain's vasculature allowed for differentiation of normal brain and tumor tissue. Moreover, with a spatial resolution of optical images below 20 $\mu m^2$/pixel, even small areas of residual tumor can be identified. Further, tumor tissue was identified through intact rat skull, providing a method and a device for tumor imaging prior to surgery.

Without being bound by theory, the dynamic differences in dye perfusion through normal brain tissue surrounding and tumor tissue could be accounted for by any one or a combination of the following four reasons: (1) greater extravasation of the dye through leaky tumor capillaries; (2) more rapid uptake of the dye by tumor tissue; (3) slower transit times through tumor tissue; and (4) preferential uptake of the dye by tumor cells.

The rat glioma model has been examined and microvasculature compared to normal cortex. Blood flow in tumor tissue is slower and more variable than in normal tissue. The difference between tumor and normal brain have been attributed to tumor location, degree of infiltration, and necrosis. In other studies using cultured spheroids of C6 astroglial cells transplanted into rat brain, blood flow was slower in viable tumor than in normal rat brain. Microvessel volume fraction was equivalent between tumor and normal brain. However, since only about 50% of the tumor was actively perfused, the surface area of perfused microvessels in the tumor was one-half that of the normal brain. These changes could account for a slower flow of dye through the tumor compared to normal brain and also lead to more rapid clearance by the normal brain in contrast to the tumor.

The permeability of tumor capillaries is much higher than in normal brain. Leakiness of these capillaries leads to extravasation of larger particles resulting in edema and an increase in interstitial pressure surrounding tumor microvessels. Since tumor microvessels do not contain normal arteriole smooth muscle, they also have no local control of pressure gradients. This leads to a stasis of flow in tumor tissue. The overall effect on dye perfusion is longer transit times than in normal brain and an increase which prolongs duration of the large optical signal from tumor tissue. Such reasoning supports the dynamic changes in optical signal from tumor and normal brain that was seen during dye perfusion. There is nearly equivalent uptake, but a much slower transit time in tumor tissue resulting in prolonged increases in optical signal. Also, tissue surrounding the tumor is expect to have increases in interstitial pressures but without leaky capillaries and other microvasculature changes, accounting for the fact that tumor tissue had an intermediate duration of optical changes.

It is not clear whether a more rapid clearance mechanism of the dye from normal brain was occurring or if the dye was being preferentially sequestered by tumor cells. In the later case, hematoporphyrins are preferentially taken up into tumor cells, and accounts for the ability to use photodynamic therapy on such cells. If the dye remained completely intravascular, then a very uneven distribution of dye between normal and tumor cells would be expected. However, we observed the opposite from many intermediate images taken from areas between larger pial microvessels.

The present invention further provides a method for imaging of cortical functional areas and dysfunctional areas, such as those areas of severe epileptic activity. The method involves administering a sensory signal for mapping a particular cortical function, or identifying an area of hyperactivity that is the location of epileptic activity in an epileptic patient. An epileptigenic area of the cortex will be visualized as spontaneously more active and can be imaged by the inventive apparatus using a method for mapping intrinsic signals of cortical activity.

The method for visualizing intrinsic signals involves stimulating cortical tissue with specific paradigms. Various paradigms include, for example, presenting pictures of objects to a patient and asking the patient to name the object to alter neuronal activity which will result in an associated intrinsic signal.

Another feature of the inventive apparatus and method is the ability to image peripheral nerve damage and scarring. Nerves of the central and peripheral nervous system (PNS) are characterized by the ability to regenerate after damage. During operations to repair damaged peripheral or cranial nerves, one can image areas of nerve damage by imaging areas of blockage of intrinsic signals. For example, the nerve is exposed in the area of interest. The nerve is stimulated upstream of the site of damage. The active nerve pathway is imaged by intrinsic signals in the processed difference frame after activation. The site of nerve damage or blockage is evidenced by an abrupt end or diminution to the intrinsic signal at the damage site. In this way, the surgeon is able to obtain real time information precisely where there is nerve damage and to correct the damage, if possible.

Moreover, the inventive apparatus and ability to image intrinsic signals can be used when there is a need to remove tumor tissue that is located surrounding or adjacent to nerve tissue. For example a tumor called an acoustic neuroma is usually located surrounding an auditory (hearing) nerve. It is often a difficult procedure to remove tumor tissue without severing the auditory nerve (a cranial nerve) and causing one ear to become deaf or damage the facial nerve that innervates muscles that move the face. The inventive methods provide an ability to distinguish tumor tissue from surrounding nerve tissue using a dye. Additionally, the inventive method can continually provide information to the surgeon showing the precise location of the auditory or facial nerve by continually or periodically stimulating the nerve with a sound paradigm for the auditory nerve, or backfiring the facial nerve from a facial muscle, and detecting the intrinsic signal associated with nerve activity. Accordingly, when there is tumor tissue in close proximity to nerve tissue, one can use both the ability to locate tumor tissue with a dye and to locate nerve tissue by detecting intrinsic signal using the same imaging apparatus.

The imaging method can obtain information at the surface of an area of interest or can target an area of interest at a level deeper in tissue. Longer wavelengths of emr used to form the image (averaged control image and subsequent averaged images) can be used to probe areas of interest which are deeper into tissue. Moreover, if a difference image is created between the image seen with 500 nm emr and the image seen with 700 nm emr, the difference image will show an optical slice of tissue. Moreover, instead of using cutoff filters, administration of a dye can act as a tissue filter of emr to provide a filter in the area of interest. In this instance, it is desirable to utilize a dye that remains with tumor or normal tissue for a prolonged period of time.

The present invention further comprises a method for enhancing sensitivity and contrast of the images obtained from tumor tissue or intrinsic signal difference images, comprising: (a) illuminating an area of interest with a plurality of wavelengths of emr, wherein there is at least a first wavelength of emr and a second wavelength of emr; (b) obtaining a series of frames corresponding to each wavelength of emr, wherein a first sequence of frames is from the first wavelength of emr, the second sequence of frames is from the second wavelength of emr and so on; (c) processing the first sequence of frames into a first averaged control image, the second sequence of frames into a second averaged control image and so on; (d) stimulating for intrinsic signals or administering a dye for tumor tissue imaging; (e) obtaining a first series of subsequent frames using the first wavelength of emr, a second series of subsequent frames using the second wavelength of emr, and so on, and processing the first, second and so on subsequent series of frames into the first, second and so on subsequent averaged images, respectively; (f) obtaining a first difference image by subtracting the first averaged control image from the first subsequent averaged image and a second difference image by subtracting the second averaged control image from the second subsequent averaged image, and so on; and (g) obtaining an enhanced difference image by ratioing the first difference image to the second difference image. This can be accomplished, for example, with two single wavelength sources of emr, or by using a broad multiple wavelength source of emr and a plurality of longpass filters. Preferably, the monochromatic emr to illuminate the area of interest are from laser sources.

The inventive apparatus and methods for imaging intrinsic signals and tumor tissue can operate outside of a surgical procedure setting. More specifically, it is possible to obtain tissue imaging through intact skin and bone. In some areas of the body longer wavelength visible light and near infrared emr can easily pass through such tissue for imaging, such as breast tissue. With dye injection, areas of increased vascularity, such as tumor tissue can be identified.

Yet another aspect of the inventive method involves using an emr absorbing or fluorescent dye conjugated to a targeting molecule, such as an antibody, or more particularly, a monoclonal antibody or fragment thereof specific for an antigen surface marker of a tumor cell. The area of interest is illuminated with emr containing excitation wavelengths of the fluorescent dye but not emission wavelengths. This can be accomplished by use of a cutoff filter over the emr source. Preferably, the CCD camera is coupled to an image intensifier or micro channel plate (e.g., KS-1381 Video Scope International, Wash D.C.) to increase the sensitivity of the system by several orders of magnitude and allow for visualization of cells having fluorescent dyes attached hereto. Examples of fluorescent dyes that can be conjugated to a targeting molecule include, for example, Cascade Blue, Texas Red and Lucifer Yellow CH from Molecular Probes Eugene, Ore.

Still further applications of the inventive device are possible. For example, the device can be used for calibration of electrodes used to electrically stimulate the cortical surface (see, for example, FIGS. 1 and 2). A technique presently used by surgeons to map the functional organization of an awake patients cortex is to directly apply current (via stimulating-electrodes) to the surface of the cortex. The surgeon would like to apply the greatest intensity of stimulating current as possible without triggering an epileptic seizure or causing tissue damage. As a method of calibrating the stimulating-electrodes, the surgeon stimulates the cortex of the patient with currents of varying intensities and monitors the electrical activity by observing the output of recording-electrodes which have been placed directly on the surface of the patients brain. The surgeon applies current for several seconds with the stimulating-electrodes and checks the output from the recording-electrodes for afterdischarge epileptiform activity which may persist for a period of time after stimulation has ceased. The inventive device provides an accurate means of monitoring spatial extent of the cortex affected by the electrode stimulation current, and time course (if any) of stimulation-evoked activity persisting after cessation of the stimulation current. The method comprises acquiring a control image prior to stimulation, and then acquiring subsequent images during and alter stimulation. The images are processed as described herein to provide a highly resolved spatial map of those areas of the cortex whose resting activity has been affected by the applied stimulating current. The inventive device provides a map of the spatial extent and timecourse of stimulation and epileptic activity, which the surgeon can use to choose an appropriate stimulating current for his or her electrodes.

It is also possible to utilize the inventive device for simultaneous spatial mapping of dynamic changes of blood-flow in blood vessels and cortical activity using intrinsic optical changes. (see, for example, FIGS. 1 and 2) Without being bound by theory, the intrinsic optical changes within regions of larger blood vessels are due to a rate of change of the flow-rate within these vessels. The invention provides a method for monitoring these changes of flow within individual blood vessels.

It is also possible to utilize the inventive device for a method to map functional organization of the cortex in an anesthetized patient during a neurosurgical procedure. (see, for example, FIG. 5) A method comprises providing an afferent sensory stimulation to activate an area of cortex specific to processing this afferent sensory input, and using the evoked intrinsic signals observed with the inventive device and method to optically map regions of the cortex involved in the afferent sensory stimulation.

For example, during surgical removal of a tumor, the surgeon may need to know which area of cortex is involved in processing sensory input from a limb in an anesthetized patient. The surgeon can apply an afferent sensory input, such as a vibrating stimulus, to the limb to cause the conduction of information to that part of the cortex involved in sensory processing for this limb. This sensory stimulus will activate the appropriate region of cortex which can then be mapped using the inventive device and method. Other examples of afferent sensory input include providing sound stimuli to activate auditory cortex, visual stimuli to map visual cortex, moving a joint, etc. This method is useful for mapping certain functional areas in an anesthetized patient.

It is also possible to utilize the inventive device for a method to aid the surgeon intraoperatively in the acquisition of biopsies from a tumor margin. (see, for example, FIG. 12). After the surgical removal of a tumor, the surgeon is left with the task of trying to distinguish what areas of the tumor resection margin contain remnants of tumor tissue. This is important since it is thought that in many tumor types, the effectiveness of post-operative radiation and chemotherapy is correlated to the amount of tumor tissue left behind. The present technique of identifying these remnants of tumor is for the surgeon to remove small amounts of tissue in a random sampling fashion and send these samples for analysis to a pathologist. This sampling and analysis must occur during the course of the surgery, since the surgeon needs this information to base his or her surgical decisions as to what tissue should be further resected. This technique suffers from several drawbacks, such as, the time required increases the length of the surgery thus increasing the cost and risk to the patient, and the random sampling method of determining biopsy sights is inevitably fraught with sampling error. The present invention provides a method for quickly determining the likely sites of remnant tumor tissue within a tumor margin. This can assist a surgical decision as to what areas of tissue should be sampled for biopsy purposes and which areas should be immediately removed a likely containing tumor tissue.

EXAMPLE 1

This example illustrates optical changes on a human subject by direct cortical electrical stimulation. Surface electrical recordings (surface EEG, ECOG) were correlated with optical changes. FIGS. 1 and 2 illustrate dynamic changes in intrinsic optical properties of human cortex during direct electrical stimulation of the cortex and during epileptiform activity. Figures A, B, C, and D, exemplify a typical optical imaging study where the inventive device is utilized to provide dynamic information with high spatial resolution of the intrinsic optical changes of the human cortex during either awake or anesthetized neurological surgical procedures. In FIG. 1, intrinsic optical changes were evoked in an awake patient during stimulating-electrode "calibration". Four stimulation trials were sequentially applied to the cortical surface, each stimulation evoking an epileptiform afterdischarge episode. A stimulation trial consists of: 1) monitoring resting cortical activity by observing the output of the recording electrodes for a brief period of time, 2)applying and electric current via the stimulation-electrodes to the cortical surface at a particular current for several seconds, and 3) monitoring the output of the recording electrodes for a period of time after stimulation has ceased.

A series of images (each image consisting of an average of 128 frames acquired at 30 Hz) were acquired during each of the four stimulation trials. A current of 6 mA was used for the first three stimulation trials, and 8 mA for the fourth. After a sequence of 3–6 averaged control images were acquired, a bipolar cortical stimulation current was applied (either 6mA or 8 mA) until epileptiform after discharge activity was evoked (as recorded by the surface electrode). Images were continuously acquired throughout each of the four stimulation trials.

The percentage change in absorption of light for each pixel was calculated for each image acquired during the four stimulation trials. The average percentage changes over the four areas (indicated by the four square regions marked in FIG. 1 A) were plotted graphically in FIGS. 1 B, 1 C, and 1D for comparison and analysis of the dynamic changes occurring in these four spatial areas.

FIG. 1A is a view of a human cortex just anterior to face-motor cortex with one recording electrode (r) and two stimulating electrodes (s), and four sites (the boxed areas labeled 1, 2, 3, and 4) where the average percent changes of absorption over these areas were determined. The cortex was illuminated with emr >690 nm. The scale bar is 1 cm.

Figure 1B:
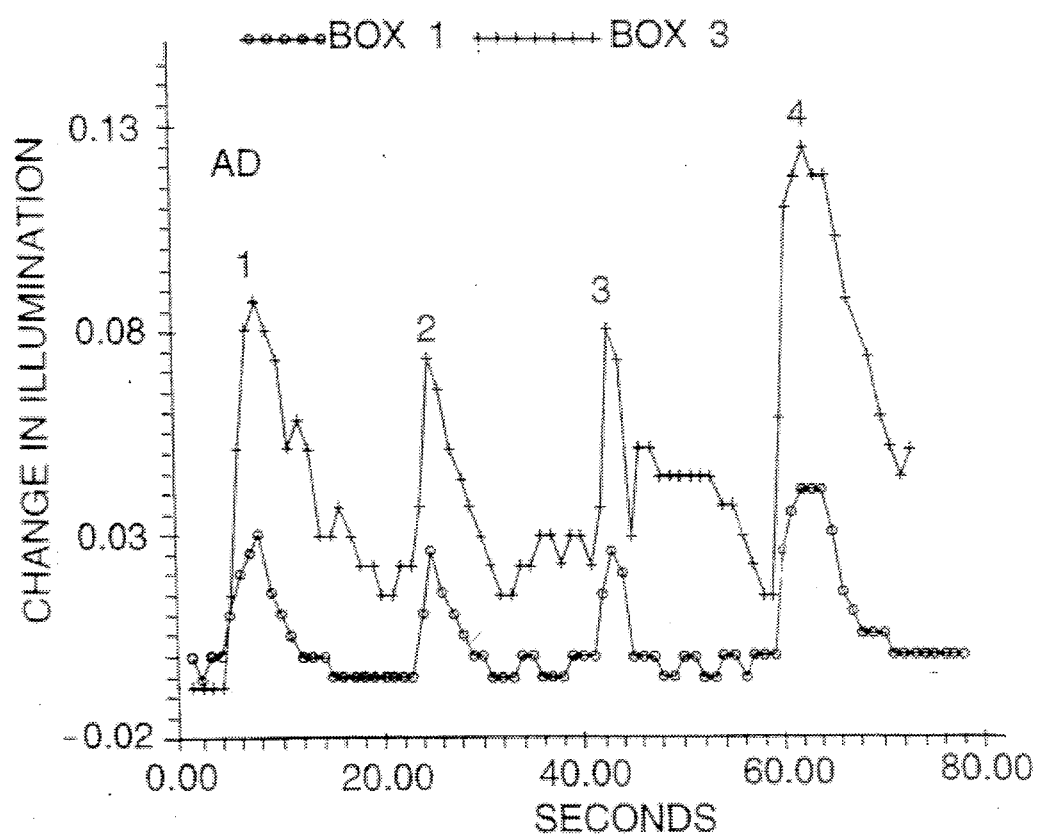
FIG. 1B shows plots of the percent change of emr absorption per second in the spatial regions of boxes 1 and 3 (as labeled in FIG. 1A). For both regions, the peak change is during the fourth stimulation trial (at 8 mA) in which the greatest amount of stimulating current had induced the most prolonged epileptiform afterdischarge activity. The changes within box 3 were greater and more prolonged than those of box 1. Box 3 was overlying the area of the epileptic focus (the excitable area of tissue possibly responsible for the patient's epilepsy).

FIG. 1B are plots of the percent change of emr absorption per second in the spatial regions of boxes 1 and 3 (as labeled in FIG. 1A). For both regions, the peak change is during the fourth stimulation trial (at 8 mA) in which the greatest amount of stimulating current had induced the most prolonged epileptiform afterdischarge activity. The changes within box 3 were greater and more prolonged than those of box 1. Box 3 was overlying the area of the epileptic focus (the excitable area of tissue possibly responsible for the patients epilepsy).

Figure 1C:
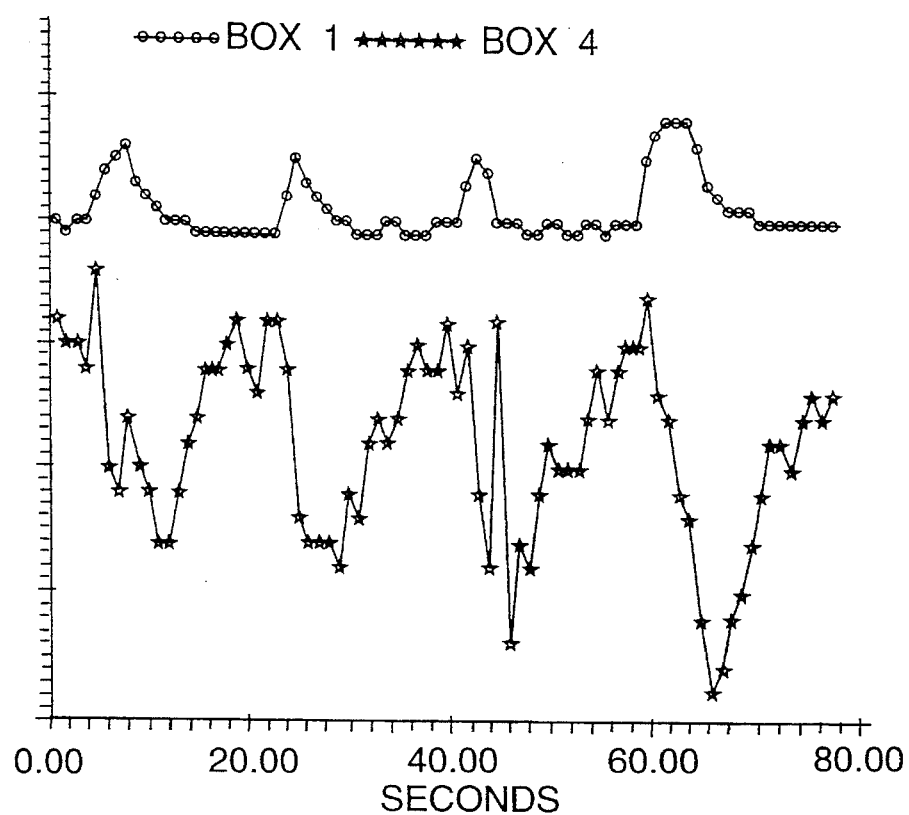
FIG. 1C show plots of the percent change of emr absorption per second in the spatial regions of boxes 1 and 4 (as labeled in FIG. 1A). Box 1 overlays and area of cortical tissue between the two stimulating electrodes, and box 4 overlays a blood vessel. The changes within box 4 are much larger and in the opposite direction of box 1. Also these changes are graded with the magnitude of stimulating current and afterdischarge activity. Since the changes in box 4 are most likely due to changes of the blood-flow rate within a blood vessel, this plot shows that the invention can simultaneously monitor cortical activity and blood-flow.

FIG. 1C show plots of the percent change of emr absorption per second in the spatial regions of boxes 1 and 4 (as labeled in FIG. 1A). Box I overlays and area of cortical tissue between the two stimulating electrodes, and box 4 overlays a blood vessel. The changes within box 4 are much larger and in the opposite direction of box 1, and also that these changes are graded with the magnitude of stimulating current and afterdischarge activity. Since the changes in box 4 are most likely due to changes of the blood-flow rate within a blood vessel, this plot shows that the invention can simultaneously monitor cortical activity and blood-flow.

Figure 1D:
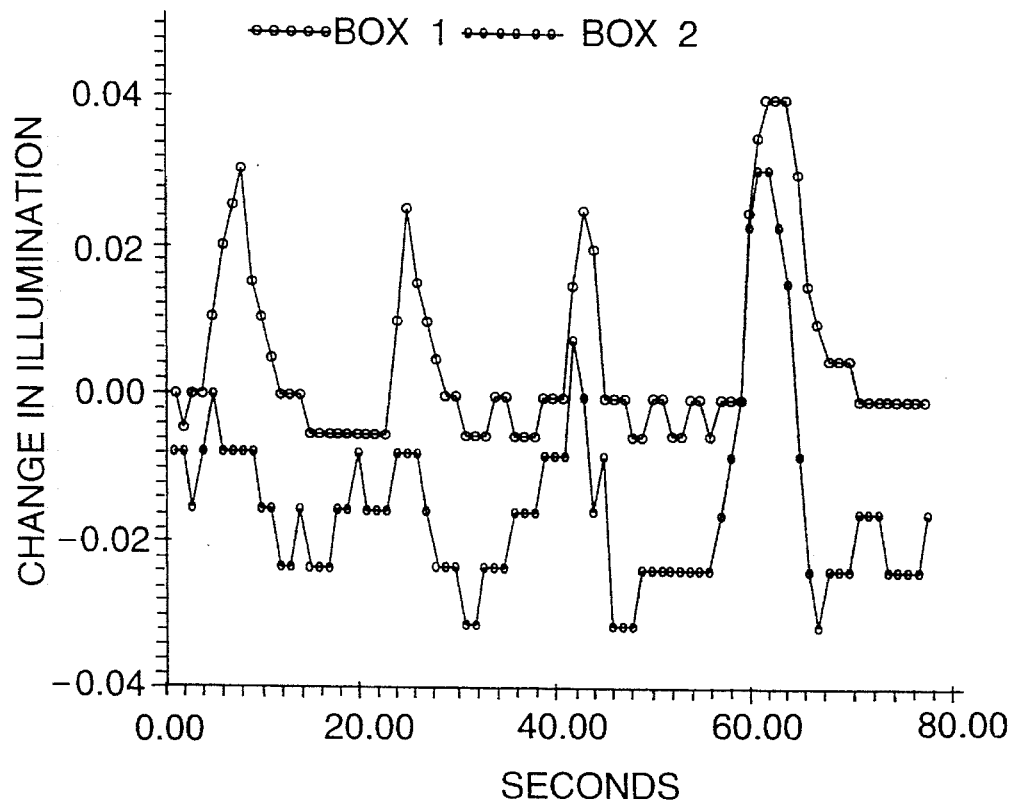
FIG. 1D shows plots of the percent change of emr absorption per second in the spatial regions of boxes 1 and 2 (as labeled in FIG. 1A). Note that although these two areas are nearby each other, their optical changes are in the opposite direction during the first three stimulation trials using 6 mA current. The negative going changes within the region of box 2 indicate that the invention may be used to monitor inhibition of cortical activity as well as excitation.

FIG. 1D shows plots of the percent change of emr absorption per second in the spatial regions of boxes 1 and 2 (as labeled in FIG. 1A). Note that although these two areas a nearby each other, their optical changes are in the opposite direction during the first three stimulation trials using 6 mA current. The negative going changes within the region of box 2 indicate that the invention may be used to monitor inhibition of cortical activity as well as excitation.

All imaging procedures reported in this example and the patient consent form were reviewed and approved by the University of Washington Human Subjects Review Committee. All patients signed an informed consent statement for both the surgery and the imaging experiments. The cortex was evenly illuminated by a fiberoptic emr passing through a beam splitter, controlled by a D.C. regulated power supply (Lambda, Inc.) and passed through a 695 nm longpass filter. Images were acquired with a CCD camera (COHU 6500) fitted to the operating microscope with a specially modified cineadaptor. The cortex was stabilized with a glass footplate. Images were acquired at 30 Hz and digitized at 8 bits (512×480 pixels, using an Imaging Technology Inc. Series 151 system, Woburn, Mass.). Geometrical transformations were applied to images to compensate for small amounts of patient motion (Wohlberg, *Digital Imaging Warping*, I.E.E.E. Computer Society, Los Alamitos, Calif., 1988). Subtraction of images collected during the stimulated state (e.g., during cortical surface stimulation, tongue movement, or naming) from those collected during a control state with subsequent division by a control image resulted in percentage difference maps. Raw data (i.e., no digital enhancement) were used for determining the average optical change in specified regions (average sized boxes was 30×30 pixels or 150–250 $\mu m^2$). For pseudocolor images, a linear low pass filter removed high frequency noise and linear histogram transformations were applied. Noise was defined as the standard deviation of fluctuations in sequentially acquired control images as 0.003–0.009.

The optical changes between the stimulating electrodes (site # 1 in FIG. 1A) and near the recording electrode (site #3 ) showed a graded response to the intensity and duration of each afterdischarge episode (FIG. 1B). The spatial extent of the epileptiform activity was demonstrated by comparing a baseline image collected before stimulation to those obtained immediately after stimulation. The intensity and spread of the optical changes were much less following stimulation #2 (shortest least intense afterdischarge episode) than after stimulation #4 (longest most intense afterdischarge episode).

When the optical changes were below baseline, the surface EEG recordings did not identify epileptiform activity (n=3 patients) At site #3 in FIG. 2A1, the optical changes after stimulation were below baseline (i.e., black regions in FIG. 2A3). However, during the fourth stimulation, the epileptiform activity spread into the area of site #3 and the optical signal did not go below baseline until later (site #3, FIG. 1B). This negative optical signal likely represents inhibited neuronal populations (an epileptic inhibitory surround), decreased oxygen delivery, or blood volume shunted to activated regions.

FIG. 3 shows a sequence of dynamic changes of optical signals identifying active areas and seizure foci. This Figure shows eight percentage difference images from the stimulation trial 2 described in the previous two Figures. Each image captures a two second interval. Note the focal area of greatest optical change in the center of images 4, 5, and 6 that indicates the region of greatest cortical activity. The magnitude of optical change is indicated by the gray-scale bar in FIG. 2. Each image maps an area of cortex approximately 4 cm by 4 cm.

FIG. 4 illustrates a real-time sequence of dynamic changes of stimulation-evoked optical changes in human cortex. FIG. 4, panels 1 through 8, show eight consecutive percentage difference images, each image is an average of 8 frames (<¼ second per image). Each image maps to an area of cortex that is approximately 4 cm by 4 cm.

In FIG. 6, stimulation mapping of the cortical surface was performed on awake patients under local anesthesia to identify sensory/motor cortex and Broca's areas. During three "tongue wiggling" trials images were averaged (32 frames, 1 sec) and stored every 2 seconds. A tongue wiggling trial consisted of acquiring 5–6 images during rest, then acquiring images during the 40 seconds that the patient was required to wiggle his tongue against the roof of his mouth, and then to continue acquiring images during a recovery period. The same patient was then required to engage in a "language naming" trial. A language naming trial consisted of acquiring 5–8 images during rest (control images—the patient silently viewing a series of blank slides), then acquiring images during the period of time that the patient engaged in the naming paradigm (naming a series of objects presented with a slide projector every 2 seconds, selected to evoke a large response in Broca's area), and finally a series of images during the recovery period following the time when the patient ceased his naming task (again viewing blank slides while remaining silent). Images A1 and B 1 are gray-scale images of an area of human cortex with left being anterior, right-posterior, top-superior, and the Sylvan fissure on the bottom. The two asterisks on A1, B 1, A2, and B2 serve as reference points between these images. The scale bars in the lower right corner of A1 and B1 are equal to 1 cm. In A1, the numbered boxes represent sites where conical stimulation with electrical stimulating electrodes evoked palate tingling (1), tongue tingling (2), speech arrest-Broca's areas (3,4) and no response (11,12, 17, 5-premotor). Image A2 is a percentage difference control image of the cortex during rest in one of the tongue wiggling trials. The gray-scale bar on the right of A2 shows the relative magnitude of the gray scale associated with images A2, A3, B2 and B3. Image A3 is a percentage difference map of the peak optical changes occurring during one of the tongue wiggling trials. Note that areas identified as tongue and palate sensory areas by conical stimulation show a large positive change. The suppression of baseline noise in surrounding areas indicate that, during the tongue wiggling trials, language-motor areas showed a negative going signal. Image B2 is a percentage difference control image of the cortex during one of the language naming trials. Image B3 is a percentage difference image of the peak optical change in the cortex during the language naming task. Large positive going signals are present in Broca's area, however negative going signals are present in tongue and palate sensory areas.

Figure 7A:
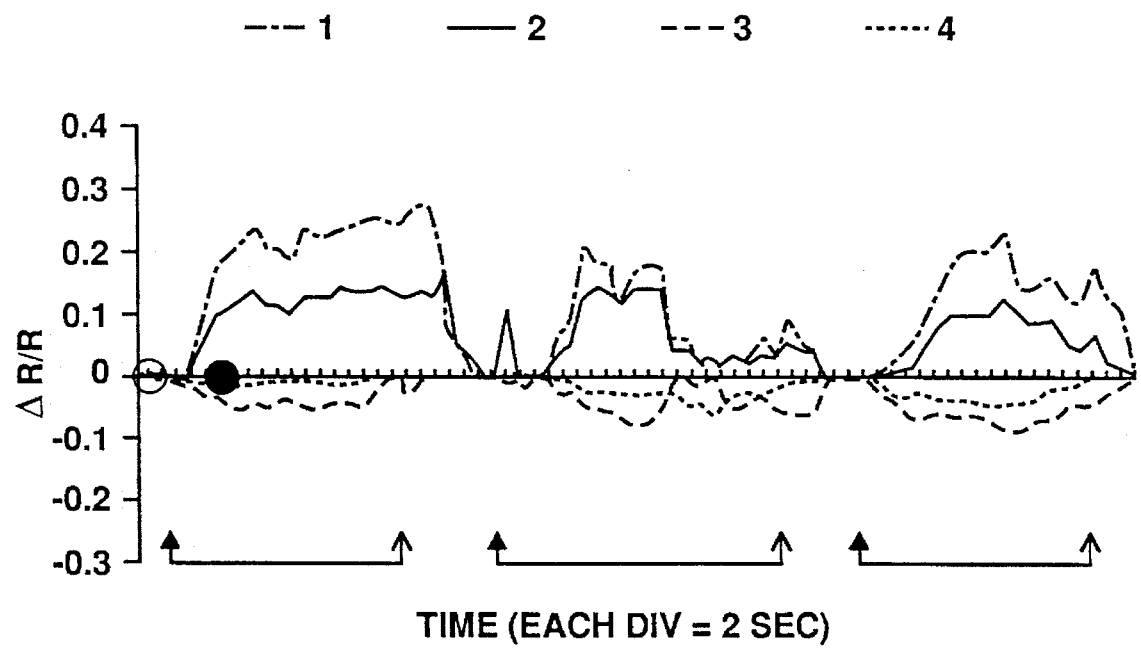
FIG. 7A shows the plots during the three tongue wiggling trials averaged spatially within the boxes 1, 2, 3, and 4 as identified in FIG. 6, A1.
Figure 7B:
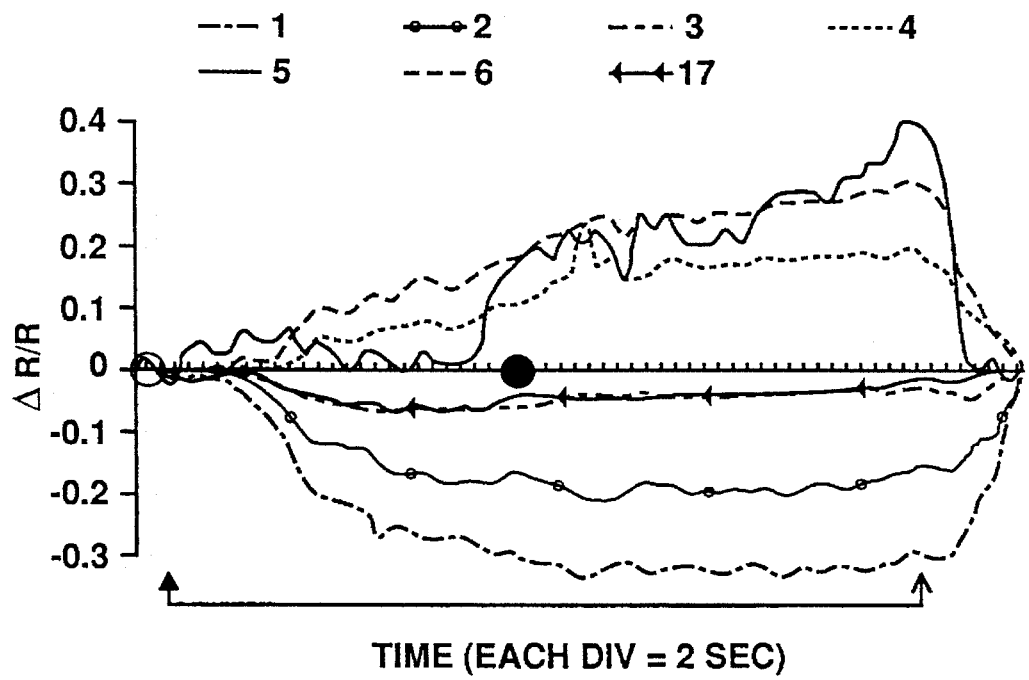
FIG. 7B shows the plots during one of the language naming trials averaged spatially within the boxes 1–7 and 17.

FIG. 7 shows a time course and magnitude plot of the dynamic optical changes in human cortex evoked in tongue and palate sensory areas and in Broca's area (language). FIG. 7 shows the plots of the percentage change in the optical absorption of the tissue within the boxed regions shown in FIG. 6, images A1 and B1, during each of the three tongue wiggling trials and one of the language naming trials. Diagram 7A shows the plots during the three tongue wiggling trials averaged spatially within the boxes 1, 2, 3, and 4 as identified in FIG. 6, image A1. Diagram 7B shows the plots during one of the language naming trials averaged spatially within the boxes 1–7 and 17. These results agree with those data reported by Lee et al. (*Ann. Neurol.* 20:32, 1986) who reported large electrical potentials in the sensory cortex during finger movement. The magnitude of the optical changes in the sensory cortex during tongue movement (10–30%) parallels sensory/motor cortex studies where cerebral blood flow increases 10– 30% during motor tasks (Colebatch et al., *J. Neurophysiol.* 65: 1392, 1991 ). Further, utilizing Magnetic Resonance Imaging (MRI) of blood volume changes in human visual cortex during visual stimulation, investigators have demonstrated increases of up to 30% in cerebral blood volume (Belliveau et al., *Science* 254:716, 1991).

Optical images were obtained from this same conical region (i.e., area of interest) while the patient viewed blank slides and while naming objects on slides presented every two seconds. Percentage difference maps obtained during naming showed activation of the premotor area. The sites of speech arrest and palate tingling were identified by surface stimulation and demonstrate optical signals going in the opposite direction. The area of activation was clearly different from that evoked by tongue movement without speech production. The optical images of premotor cortex activation during naming were in similar locations to the cortical areas identified in PET single word processing studies (Peterson et al., *Nature* 331:585, 1991; Frith et at., *J. Neuropsychologia* 29:1137, 1991). The optical changes were greatest in the area of the cortex traditionally defined as Broca's area and not in areas where electrical stimulation caused speech arrest.

Figure 8A:
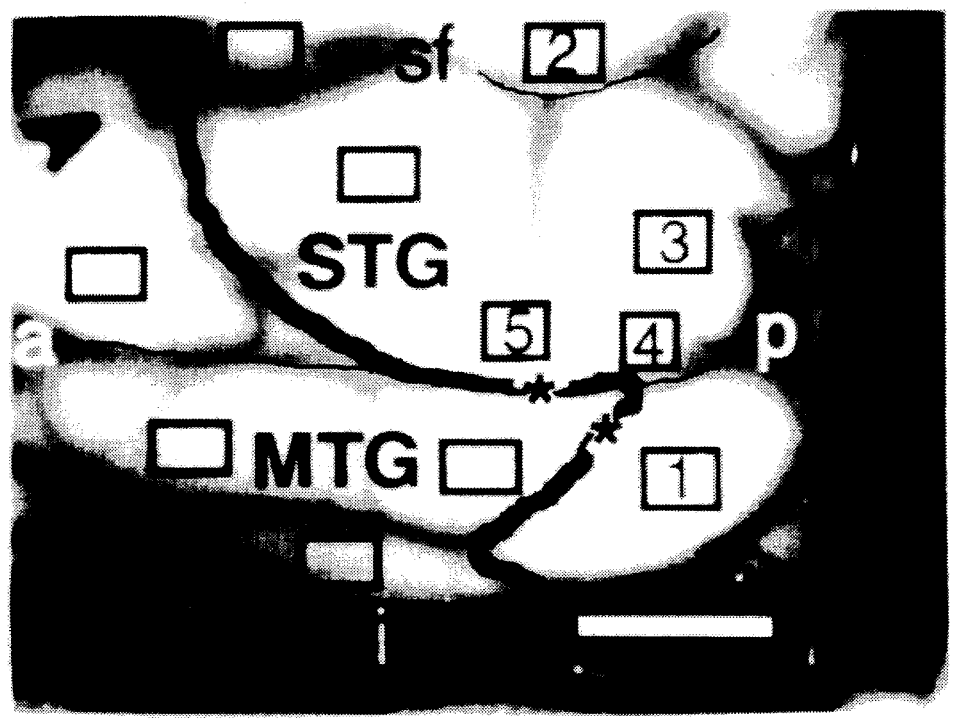
FIG. 8 illustrates an optical map of a cortical area important for language comprehension (Wernicke's area) in an awake human. Image 8A shows the cortical surface of a patient where the anatomical orientation is left-anterior, bottom-inferior, with the Sylvan fissure running along the top. After optical imaging, all cortical tissue to the left of the thick line was surgically removed. Sites #1 and #2 were identified as essential for speech (e.g., cortical stimulation blocked ability of subject to name objects). At site #3, one naming error in 3 stimulation trials was found. As the surgical removal reached the area labeled by the asterisks on the thick line, the patient's language deteriorated. All the unlabeled sites in FIG. 8A had no errors while naming slides during cortical stimulation. Image 8B shows an overlay of a percentage difference image over the gray-scale image of the cortex acquired during a language naming trial (see, FIG. 6 for description of the language naming trial). The magnitude of the optical change is shown by the gray-scale bar on the lower fight of the image. This image demonstrates how a surgeon might use this invention intraoperatively to map language cortex.
Figure 8B:

FIG. 8 illustrates an optical map of a cortical area important for language comprehension (Wernicke's area) in an awake human. FIG. 8 image A shows the cortical surface of a patient where the anatomical orientation is left-anterior, bottom-inferior, with the Sylvan fissure running along the top. After optical imaging, all cortical tissue to the left of the thick black line was surgically removed. Sites # 1 and #2 were identified as essential for speech (e.g., cortical stimulation blocked ability of subject to name objects). At site #3, one naming error in 3 stimulation trials was found. As the surgical removal reached the area labeled by the asterisks on the thick line, the patient's language deteriorated. All the unlabeled sites in FIG. 8A had no errors while naming slides during cortical stimulation. FIG. 8, image B shows an overlay of a percentage difference image over the gray-scale image of the cortex acquired during a language naming trial (see description for FIG. 6 for description of the language naming trial). The magnitude of the optical change is shown in the gray-scale bar on the lower right of the image. This image demonstrates how a surgeon might use this invention intraoperatively to map language cortex.

Figure 9A:
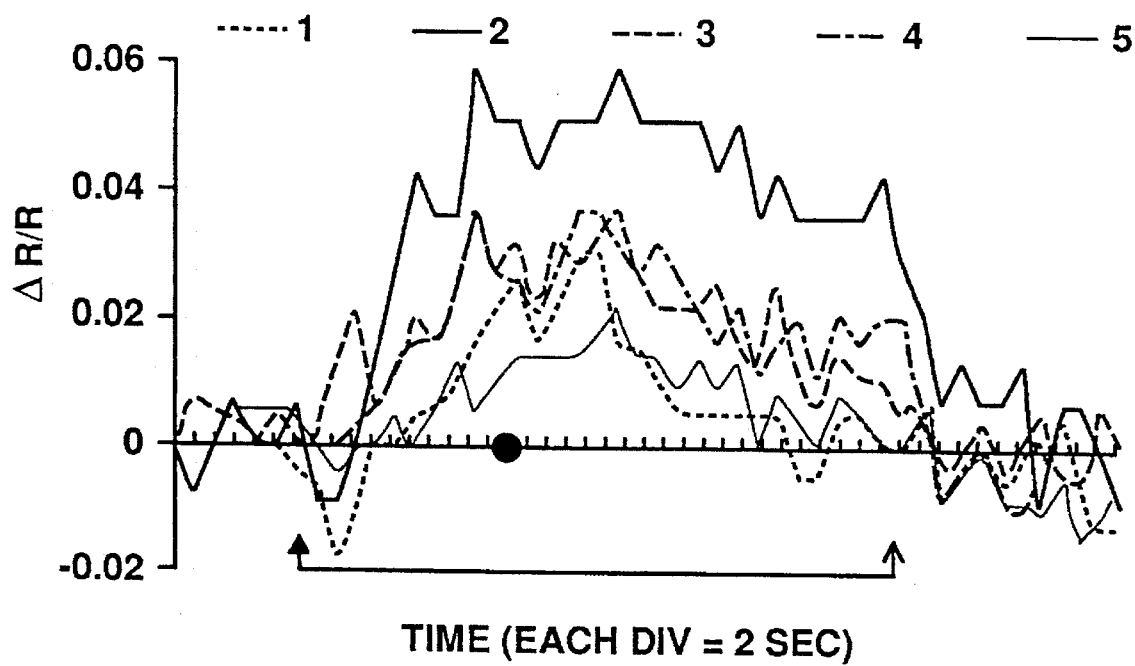
FIG. 9A shows plots of percentage change in optical absorption of tissue within the boxed regions shown in FIG. 8. The plots of boxes 1 and 2 overlay essential language sites, and boxes labeled 4, 5, and 6 overlay secondary language sites. Each of these five sights showed significant/changes occurring while the patient was engaged in a language naming task.
Figure 9B:
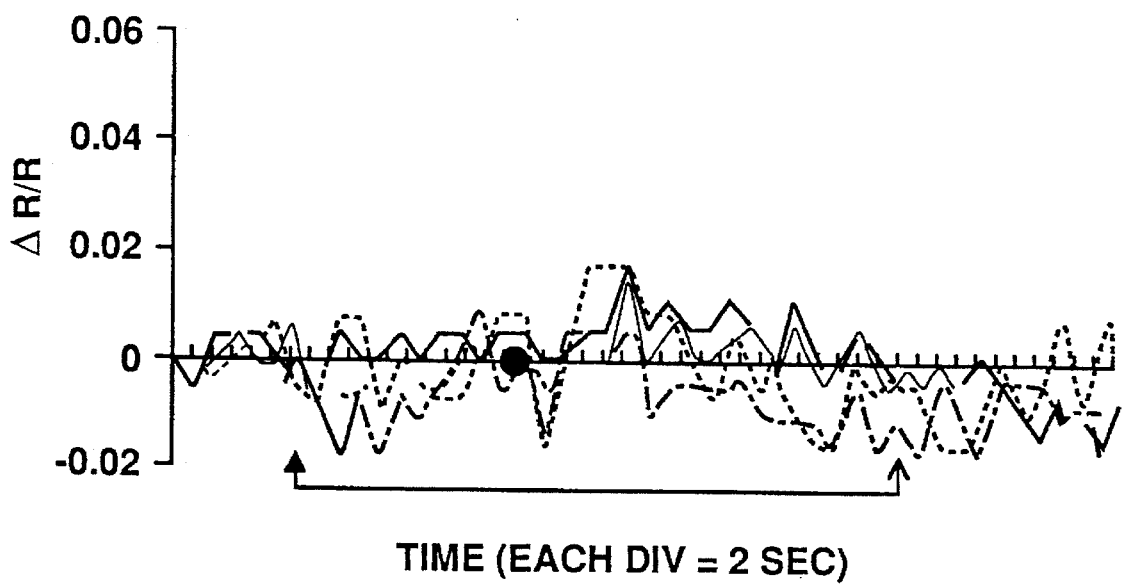
FIG. 9B shows percentage changes from the six unlabeled boxes shown in FIG. 8. There were no significant increases or decreases within these anterior sites.

FIG. 9 illustrates a time course and magnitude of dynamic optical changes in human cortex evoked in Wernicke's area (language comprehension). FIG. 9A shows plots of percentage change in optical absorption of tissue within the boxed regions shown in FIG. 8. FIG. 9A shows plots of boxes 1 and 2 overlay essential language sites, and boxes labeled 4, 5, and 6 overlay secondary language sites. Each of these five sights showed significant changes occurring while the patient was engaged in a language naming task. FIG. 9B show percentage changes from the six unlabeled boxes shown in FIG. 8. There were no significant increases or decreases within these anterior sites. These data demonstrate that optical imaging can also identify both essential and secondary language areas that must be preserved during neurosurgical procedures.

EXAMPLE 2

This example illustrates indocyanine green imaging of a low grade tumor. A MRI scan was conducted before the operation. Additionally, the patient was investigated for tumor tissue using the apparatus described according to the invention and specifically used in Example 1.

Figure 10A:
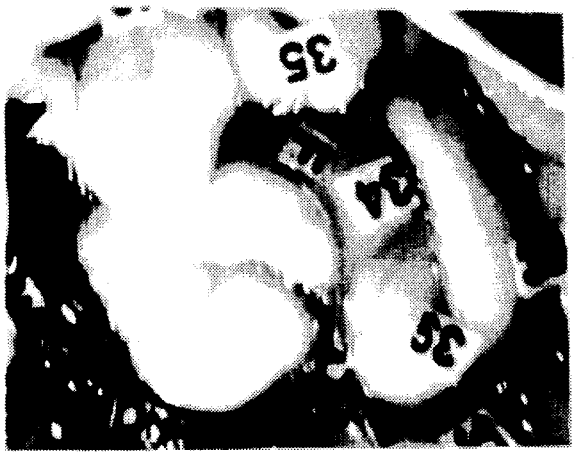
In FIG. 10A (upper left) the lettered labels placed upon the brain by the surgeon overlay the tumor as identified intraoperatively by ultrasound. However, tumors of this type and grade are notoriously difficult to distinguish from normal tissue once the surgical removal of the tumor has begun.
Figure 10D:
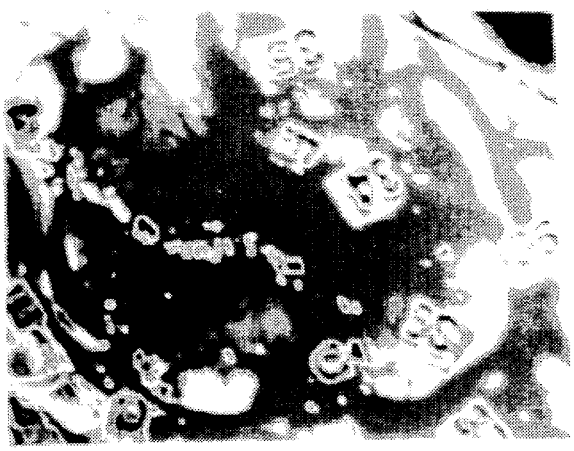
Figure 10B:
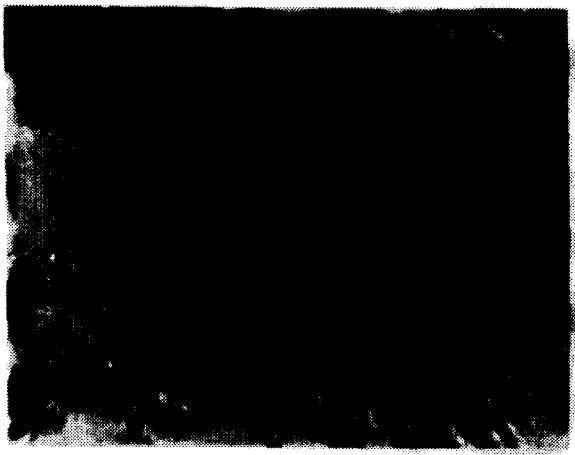
FIG. 10B (middle left) shows a difference image taken approximately 15 second,s after intravenous injection of dye (indocyanine green at 1 mg/kg).
Figure 10E:
Figure 10C:
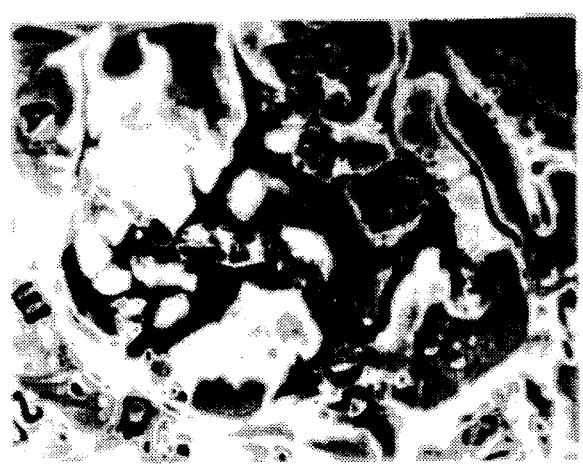
FIG. 10C (lower left) shows the difference image about 30 seconds after dye administration. The area of the tumor tissue showed the first tissue staining.
Figure 10F:
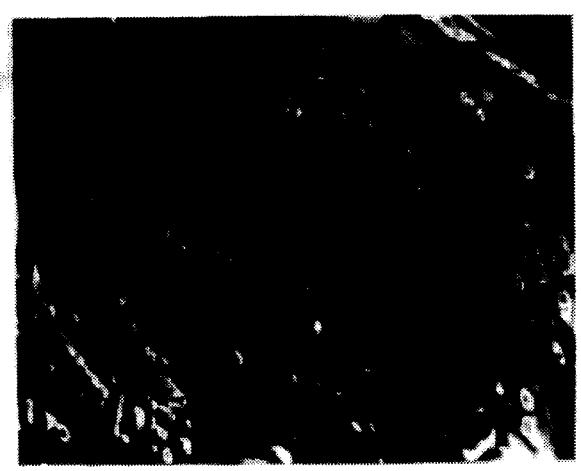

An averaged control image was obtained of the particular cortical surface area of interest. Indocyanine green dye was administered into a peripheral intravenous catheter as a bolus at time 0. FIG. 10 illustrates differential dynamics of dye to identify low grade human CNS tumor. This series of images are from a patient having a low grade CNS tumor (astrocytoma, grade 1). In FIG. 10A (upper left) the lettered labels placed upon the brain by the surgeon overlay the tumor as identified intraoperatively by ultrasound. However, tumors of this type and grade are notoriously difficult to distinguish from normal tissue once the surgical removal of the tumor has begun. FIG. 10B (middle left) shows a difference image taken approximately 15 seconds after intravenous injection of dye (indocyanine green at 1 mg/kg). FIG. 10C (lower left) shows the difference image about 30 seconds after dye administration. The area of the tumor tissue showed the first tissue staining. FIG. 10D (top right) shows that in this low grade tumor, all tissue (both normal and abnormal) showed staining at 45 sec after dye administration. FIG. 10E (middle right) is one minute after dye administration and FIG. 10F is five minutes after dye administration (showing complete clearance in this low grade tumor). These data show that indocyanine green enters low grade tumor tissue faster than normal brain tissue, and may take longer to be cleared from benign tumor tissue than normal tissue. Therefore, it is possible to image even low grade tumors with this apparatus. Furthermore, it is possible to distinguish intraoperatively low grade tumor tissue from surrounding normal tissue.

Therefore, it is possible to image even low grade tumors by the inventive apparatus. Subsequent pathology of this tumor tissue established it as a low grade glioma.

EXAMPLE 3

Figure 11A:
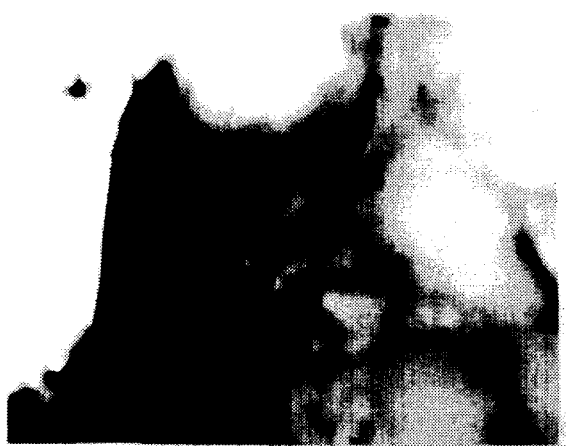
FIG. 11A (upper left) shows a gray-scale image in which malignant brain tumor tissue was densest in the center and to the fight but elsewhere was mostly normal tissue (as was shown by pathology slides and flow cytometry available one week after surgery).
Figure 11D:
FIG. 11 illustrates that differential dynamics of dye identify malignant human CNS tumor. The series of images in this Figure are from the cortex of a pat, lent with a malignant CNS tumor (glioblastoma; astrocytoma, Grade IV).
FIG. 11B (middle left) is the difference image at 15 seconds after intravenous injection of indocyanine green, showing the dynamics of dye perfusion in the first seconds in malignant tissue are similar to those in the first few seconds of benign tumor tissue (see FIG. 11C).
FIG. 11C (lower left) shows that at 30 seconds the malignant tissue is even more intense by comparison to the normal tissue. FIG: 11D (upper fight, 1 minute after dye injection) and 11E (lower fight, 10 minutes after dye injection) show that unlike benign tumor tissue, in malignant tumor tissue, dye is retained significantly longer, and in some cases, continues to sequester in the malignant tumor tissue over longer periods of time. These data illustrate a utility to identify malignant tumor tissue, distinguish intraoperatively between normal and malignant tumor tissue, and to distinguish between the various grades of tumor (e.g., normal vs. benign vs. malignant).
Figure 11B:
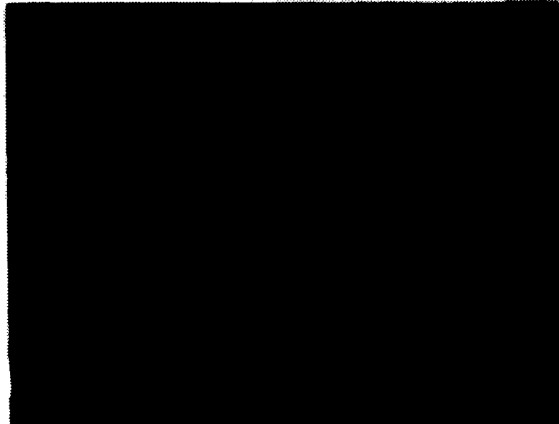
Figure 11E:
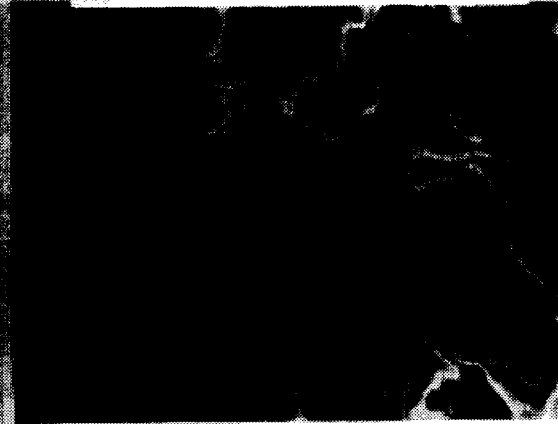
Figure 11C:

This example illustrates the image of a highly malignant CNS tumor (glioblastoma). A patient was imaged in a neurosurgical procedure as described in Example 1. The tumor imaging procedure was the same as in Example 2. The series of images in FIG. 11 are from the cortex of a patient with a malignant CNS tumor (glioblastoma; astrocytoma, Grade IV). FIG. 11A (upper left) shows a gray-scale image in which malignant brain tumor tissue was densest in the center and to the fight but elsewhere was mostly normal tissue (as was shown by pathology slides available one week after surgery). FIG. 11B (middle left) is the difference image at 15 seconds after intravenous injection of indocyanine green, showing the dynamics of dye perfusion in the first seconds in malignant tissue are similar to those in the first few seconds of benign tumor tissue (see FIG. 11C). FIG. 11C (lower left) shows that at 30 seconds the malignant tissue is even more intense by comparison to the normal tissue. FIG. 11D (upper fight, 1 minute after dye injection) and 11E (lower right, 10 minutes after dye injection) show that unlike benign tumor tissue, in malignant tumor tissue, dye is retained significantly longer, and in some cases, continues to sequester in the malignant tumor tissue over longer periods of time. Therefore, it is possible with this device to identify malignant tumor tissue, distinguish intra-operatively between normal and malignant tumor tissue, and to distinguish between the various grades of tumor (e.g., normal vs. benign vs. malignant). Thus, it is possible to not only image the location of tumor tissue, but also to grade the tumor with more malignant tumors retaining dye for a longer period of time than a lower grade tumor.

EXAMPLE 4

Figure 12A:
FIG. 12A (top left) shows a gray-scale image of the tumor margin.
Figure 12B:
FIG. 12B shows the margin with labels that the surgeon placed directly on brain. The purpose of these labels were to identify where the surgeon was going to remove biopsy samples for histological analysis after difference images were acquired with the inventive device.
Figure 12C:
FIG. 12C (lower left) shows the difference image 1 minute after intravenous injection of dye and FIG. 12D (lower right) shows the difference image 10 minutes after dye injection. These post-dye difference images reveal a number of sights that contain tumor tissue as well as areas of normal tissue. The accuracy of the optical imaging was confirmed post operatively by analysis of the biopsies. Note that a small area on the lower fight of FIG. 12D indicates a possible region of tumor tissue that would not have been biopsied by the surgeon. Hence, even in the case of extensive biopsy, the sampling error exceeds the accuracy of the invention. These data show a utility to identify small remnants of tumor tissue in a tumor margin after resection of a tumor.
Figure 12D:
FIG. 12 shows that differential dynamics of dye identify small remnants of tumor tissue in the margin of a resected malignant human CNS tumor. The images are from an area of interest where a tumor was surgically resected and biopsies were taken for multiple histological margin sampling The area of interest was thought to be free of tumor tissue after the surgical removal of the tumor. Normally, in this size of a resection margin, only a single frozen sample would be taken for pathology analysis. For the purpose of this study, five biopsies were taken from the margin to aid in correlating the histology with the map obtained by the invention.

This example illustrates a series of images taken after resection of a malignant CNS tumor until the tissue appeared to be normal. This type of imaging of tumor margins provides a novel method of real-time imaging of tumor margins. After resection, the surgeon performed multiple histological margin sampling and when waiting for frozen section results, the images shown in FIG. 13 were obtained. FIG. 13 shows a series of images and difference images of an area of interest where a tumor was resected. The area of interest was thought to be free of tumor tissue after the surgical removal of the tumor. Normally, in this size of a resection margin, only a single frozen sample would be taken for pathology analysis. For the purpose of this study, five biopsies were taken from the margin to aid in correlating the histology with the map obtained by the invention. FIG. 12A (top left) shows a gray-scale image of the tumor margin. FIG. 12B shows the margin with labels that the surgeon placed directly on brain. The purpose of these labels were to identify where the surgeon was going to remove biopsy samples for histological analysis after difference images were acquired with the inventive device. FIG. 12C (lower left) shows the difference image 1 minute after intravenous injection of dye and FIG. 12D (lower right) shows the difference image 10 minutes after dye injection. These post-dye difference images reveal a number of sights that contain tumor tissue as well as areas of normal tissue. The accuracy of the optical imaging was confirmed post operatively by analysis of the biopsies. Note that a small area on the lower right of FIG. 12D indicates a possible region of tumor tissue that would not have been biopsied by the surgeon. Hence, even in the case of extensive biopsy, the sampling error exceeds the accuracy of the invention. These data show that the invention is able to identify small remnants of tumor tissue in a tumor margin after resection of a tumor. As well, the invention could act as an aid to removing biopsies from the site of a tumor margin and reduce the innate sampling error associate with the presently used random sampling technique.

EXAMPLE 5

This example illustrates a means for setting the CCD to optimize the apparatus to be able to detect signal with maximum sensitivity across a full dynamic range. The CPU should be programmed with software having the following features: (1) an output-analog signal, values of the image are close to saturating on the bright end (i.e., close to 225) are displayed as a distinct color, such as red; (2) values that are close to the dark end (i.e., are close to zero) are also displayed as a distinct color, such as blue. The following procedure is an example of an adjustment of the CCD camera.

1. With the gain and black-level on a camera-control box (CCB) initially set to 0, increase the emr intensity until the video signal is just saturating on the bright-end (i.e., some values in the output-analog signal can be seen to be close to 255).

2. In crease the black-level on the CCB until the output image can be seen to be saturating on the dark end (i.e., some values in the output analog image can be seen to be close to 0).

3. Increase the gain on the CCB until some values of the output analog image can be seen to be saturating on the high end.

4. Iterate steps (2) and (3) until either (a) the gain is set to its maximum possible value, or (b) the black-level is set to its maximum possible value, or (c) the image is maximally enhanced across is full dynamic range (that is, no further adjustments of CCB gain, black-level or emr source will improve the image.

5. If in step (4) (a), the gain is set to its maximum level, or (b) the black-level is set to its maximum level, but the output image is still not maximally enhanced, then in the case of (a), decrease the setting on the CCB gain slightly, increase the emr source intensity until just saturating the bright end, and return to step (2). In the case of (b), decrease the setting of the black-level slightly, decrease the emr intensity, and return to step (3).

EXAMPLE 6

This example illustrates a series of experiments using a rat glioma model intraoperatively to investigate whether the inventive method and inventive device could function in an operating room setting to provide real time information to the surgeon regarding resection of all tumor tissue. The rat glioma model is a standard predictive model and was used to delineate dye uptake, clearance and overall parameters of optical imaging that result in the best images. The advantages of this model are the ability to consistently get reproducible tumors for imaging studies and to be able to respect tumor under an operating microscope and still find residual tumor with the inventive optical imaging. A disadvantage of this model is the more sarcoma-like appearance of the tumor and a lesser degree of vascularity compared to human gliomas.

Briefly, the rat glioma model uses an ethylnitrosourea-induced F-344 rat tumor line developed from a clonal population of a spinal malignant astrocytoma. This tumor is similar to human astrocytomas microscopically and in vivo, because both have stellate-shaped cells in the brain parenchyma and both have introcytoplasmic filaments 80–100 μm in diameter as seen by scanning electron microscopy. The glioma cells were maintained in Weymouth's medium supplemented with 10% fetal calf serum. Viable cells ($5\times10^4$) were trypsinized from a monolayer culture and implanted stereotaxically into the right cerebral hemisphere of 30 syngeneic female rats, each weighing 140–160 g. The stereotaxic coordinates for right frontal lobe implantation were 4.5 mm anterior to the frontal zero plane, 3 mm right from the midline and 6 mm deep. The rats were anesthetized for implantation. The heads were shaved and scalps opened, and a 1 mm burr hole made at the appropriate coordinates. The cells were injected through a 27 gauge needle, the needle left in place for 30 sec post injection and the hole was covered with bone wax. The scalp was sutured and the animals observed for 3–4 hrs until they returned to normal activity and feeding. The animals were used 10–14 days after tumor implantation. In this model, animals begin to show clinical symptoms from the tumor by 16–19 days, such as decreased activity and feeding, hemiparesis and eventually succumb between 19–27 days from mass effects due to tumor expansion.

Fourteen animals underwent complete study, including imaging before and after resection of the tumor. For study, the animals were anesthetized with 2% isoflurane, and the femoral vein canulated for administration of the dye. Anesthesia was maintained with α-chloralsoe (50 mg/kg administered ip) and urethane (160 mg/kg administered ip). The animals were placed in a stereotaxic holder. Imaging studies were then carried out before (see example 7 below) or after removal of the cranium. The tumor typically occupied the anterior one half to two thirds of the right hemisphere exposure. The compressed brain without any tumor infiltration was defined as the tumor surround to separate it from the normal hemisphere on the contralateral side. Indocyanine green was used as the intravenous dye. No dye was found in the cerebrospinal fluid after administration.

The cortical surface was first imaged, and then an operating microscope was used to attempt gross total removal of the tumor. Sites were then chosen for biopsy based on optical imaging results and later analyzed histologically. The biopsy specimens were fixed in 10% paraformaldehyde, Nissl stained and mounted. All specimens were read blindly and labeled either positive or negative for tumor. These data were correlated to the optical imaging results to identify residual tumor and statistical analysis (Chi square or student t-test) performed to determine the significance of the results.

The imaging apparatus is described herein. Light was from a tungsten-halogen bulb regulated by a D.C. power supply, passed through a longpass filter (690 nm), and through a right angled prism reflected through a 50 or 100 mm objective lens onto the cortical surface. The reflected light was collected by the same objective lens and focused by a projection lens onto the surface of a CCD camera (COHU 6300). The imaging apparatus was attached to the stereotaxic frame which was rigidly fixed to a vibration isolation table. Specially designed automatic warping algorithms were designed to compensate for small amounts of movement. Images (512×480 pixels) were acquired at 30 Hz and digitized at 8 bits (256 gray levels). Every 2 sec, a single image comprising 30 averaged frames was collected (1 sec) and then stored (1 sec). Control images were collected prior to injection of the dye and then for 2 min after dye injection. The dye injection was made over a 1 sec period while the last control image was being stored. A period of 20 min was allowed between dye injections to allow optical images to return to baseline. The initial control images of each trial were subtracted from each other to insure that the baseline starting point of each trial was equivalent.

A single control image was chosen and then subtracted from each of the controls (4–6 images) and each of the post-dye injection images. The resultant image was divided by the original control image and multiplied by 100 to give a composite percentage difference for the entire sequence before and after dye injection. The optical change that occurred between separate control images was 0.2–0.7%, whereas the peak changes resulting from dye injection were in the range of 5–40%. The control percentage difference image are represented in the attached figures. The spatial resolution of an individual pixel in the image ranged from 13.5×11.7 $\mu m^2$ to 27×25.4 $\mu m^2$. Boxes measuring from 15–30 pixels per side were drawn on the images. The average percentage change in the individual boxes was calculated and used to demonstrate graphically the optical changes over time in the different types of tissue.

Figure 16C:
FIGS. 16C and 16D show difference images of the area of interest 4 seconds and 30 seconds, respectively, after dye injection. At these intermediate stages dye appears to collect in both normal and tumor tissue.
Figure 16B:
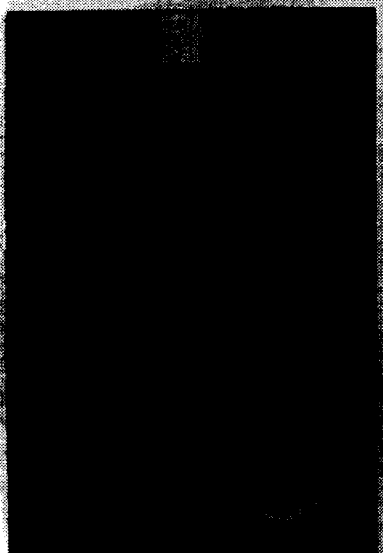
FIG. 16B shows the difference image of the area of interested 1 second after 1 mg/kg of indocyanine green had been intravenously injected into the animal. During this initial time, the tumor tissue was the first to show a measurable optical change indicating the uptake of dye occurs first in the tumor tissue. The gray-scale bar indicated the relative magnitude of the optical changes in the sequence of difference images.
Figure 16A:
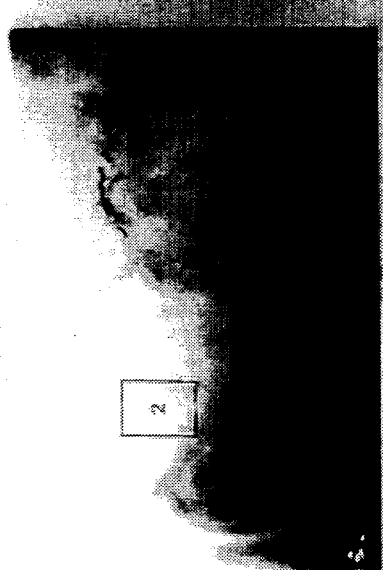
FIG. 16A shows a gray-scale image of the area of interest. This is the same animal as shown in FIG. 14, however the cranium has now been removed so as to expose the left hemisphere containing the glioma, and the right hemisphere containing normal tissue. Box 1 overlays the tumor, Box 2 the tumor-surround, and Box 3 overlays normal tissue.
Figure 16F:
FIGS. 16E and 16F show difference images of the area of interest 1 minute and 5 minutes, respectively, after injection of dye. At these later times, it becomes clear that dye was still collecting in tumor tissue even thought it was being cleared from normal tissue.
Figure 16E:
Figure 16D:

Imaging studies were performed on fourteen animals. The time course of dye perfusion through the tissue had a dynamic aspect. Optical imaging of indocyanine green dye perfusion at a dose of 1 mg/kg in 16 separate runs from a cortical surface in 9 different animals demonstrated the dynamic nature of the optical changes. FIG. 16 show a sequence of images to illustrate the dynamic differences of dye absorption changes between tumor and non-tumor tissue. FIG. 16A shows a gray-scale image of the area of interest. This is the same animal as shown in FIG. 16, however the cranium has now been removed so as to expose the left hemisphere containing the glioma, and the right hemisphere containing normal tissue. Box 1 overlays the tumor, Box 2 the tumor-surround, and Box 3 overlays normal tissue. FIG. 16B shows the difference image of the area of interested 1 second after 1 mg/kg of indocyanine green had been intravenously injected into the animal. During this initial time, the tumor tissue is the first to show a measurable optical change indicating the uptake of dye occurs first in the tumor tissue. The gray-scale bar indicate the relative magnitude of the optical changes in the sequence of difference images. FIGS. 16C and 16D show difference images of the area of interest 4 seconds and 30 seconds respectively after dye injection. At these intermediate stages dye appears to collect in both normal and tumor tissue. FIGS. 16E and 16F show difference images of the area of interest 1 minute and 5 minutes respectively after injection of dye. At these later times, it becomes clear that dye is still collecting in tumor tissue even thought it is being cleared from normal tissue.

The peak optical changes occur after 6 seconds from dye administration, but after the normal hemisphere begins to clear the dye, the tumor tissue continues to maintain a large optical due to a lack of dye clearance. These changes localize anatomically to the tumor site.

The optical signals begin to change within the first 2–3 seconds after dye injection and peak 6 seconds after injection in all three areas, tumor tissue, tumor surround and normal brain. However, the three different tissue types are differentiated by the rate of rise over the first four seconds, the peak optical change reached, and the eventual plateau that occurs after the first 30 seconds. The tumor tissue had a significantly different peak percentage difference change (40.5±9.6%) than either the tumor surround (16.4± 6.8%) or the normal brain (9.7±4.7%).

Figure 17:
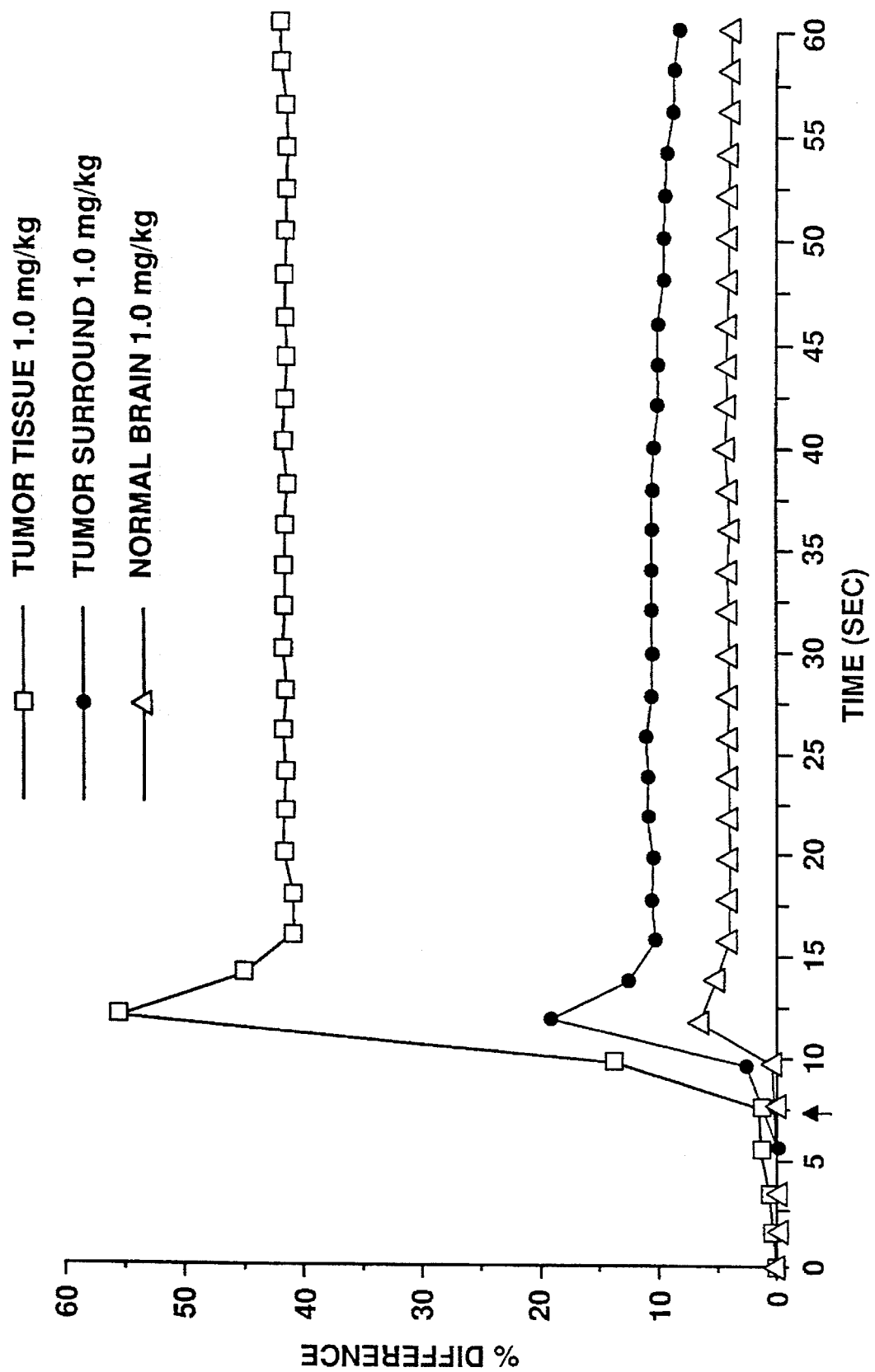
FIG. 17 shows dynamic information of dye uptake and clearance in tumor vs. non-tumor tissue. This is a plot of an average of the percentage change in emr absorption averaged over the spatial areas indicated by boxes 1, 2, and 3 from FIG. 16A. The increase in absorption was a function of the concentration of dye in the tissue at a particular time. The graph labeled "tumor tissue" is a plot of the dynamics of the absorption changes within box 1 from FIG. 16A. The graph labeled "tumor surround" is a plot of the dynamics of the absorption changes within box 2 from FIG. 16A. The graph labeled "normal brain" is a plot of the dynamics of the absorption changes within box 3 from 16A

FIG. 17 is a plot of an average of the percentage change in emr absorption average over the spatial areas indicated by boxes 1, 2, and 3 from FIG. 16A. The increase in absorption is a function of the concentration of dye in the tissue at a particular time. The graph labeled "tumor tissue" is a plot of the dynamics of the absorption changes within box 1 from FIG. 16A. The graph labeled "tumor surround" is a plot of the dynamics of the absorption changes within box 2 from FIG. 16A. The graph labeled "normal brain" is a plot of the dynamics of the absorption changes within box 3 from 16A. This data as well as that from FIG. 16 show that the inventive method and device is able to distinguish not only tumor from non-tumor tissue, but also tumor-surround areas which contain varying densities of tumor vs. normal cells.

Since the peak optical change was always reached 4-6 seconds after dye injection, there was also a significantly faster rate of optical change in the tumor tissue compared to the tumor surround or the normal brain. A more rapid onset of dye perfusion into the tumor tissue was displayed as a faster time course. The tumor tissue had a more rapid and greater rise time than either the tumor surround or normal brain ($p<0.01$).

An essential feature to be able to differentiate normal from abnormal tissue is distribution of the dye into three very different tissue compartments. In 13 of 14 animals there was a prolonged increase (>2 min) in the optical signal in the tumor after the normal and tumor surround tissue had returned to baseline. Finally, even the normal and tumor surround tissue were significantly different in dye uptake (rise time: normal 2.4%/sec; tumor surround 4.0%/sec). Therefore, the dynamic features of dye uptake and clearance are critical for determining the type of tissue involved in imaging resection margins.

Figure 18A:
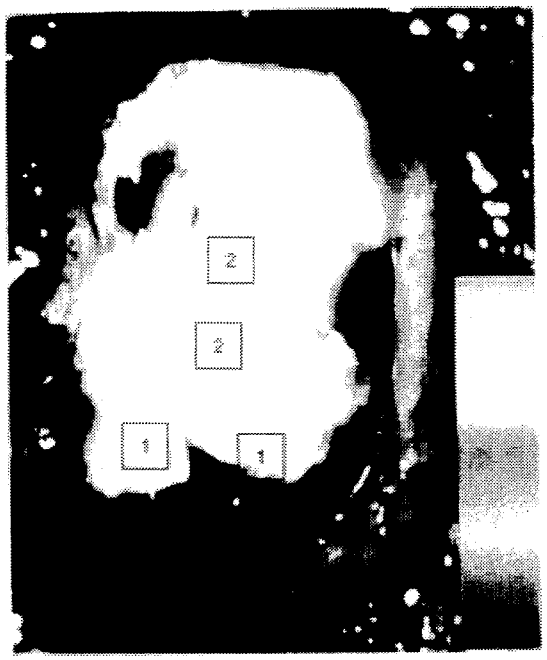
FIG. 18A shows a higher magnification image of the left hemisphere tumor margin of the animal after the tumor has been resected. Boxes 1 are over areas that contain small traces of residual tumor cells, and boxes 2 are over areas containing only normal tissue. The gray-scale bar indicates the magnitude of optical change in the difference images.
Figure 18B:
FIGS. 18B, 18C, and 18D show difference images of the tumor margin 4, 30, and 60 seconds after intravenous dye injection respectively. Minute biopsies were taken from areas that showed preferred dye containment and from areas from which the dye cleared rapidly. These biopsies were analyzed blindly and later correlated to the location from which the biopsies were taken. Those biopsies taken from areas which cleared dye were shown to contain only normal cells, whereas biopsies taken from areas which sequestered dye were shown to contain tumor cells. Extremely small islands of residual tumor can be mapped within the tumor margins.
Figure 18C:
Figure 18D:

The rat glioma model also provided an opportunity to look at imaging resection margins once all visible tumor had been removed. FIG. 18A shows a higher magnification image of the left hemisphere tumor margin of the animal after the tumor had been resected. Boxes 1 are over areas that contained small traces of residual tumor cells, and boxes 2 are over areas that contained only normal tissue. The gray-scale bar indicates the magnitude of optical change in the difference images. FIGS. 18B, 18C, and 18D show difference images of the tumor margin 4, 30, and 60 seconds after intravenous dye injection respectively. Minute biopsies were taken from areas that showed preferred dye containment and from areas from which the dye cleared rapidly. These biopsies were analyzed blindly and later correlated to the location from which the biopsies were taken. Those biopsies taken from areas which cleared dye were shown to contain only normal cells, whereas biopsies taken from areas which sequestered dye were shown to contain tumor cells. The more rapid rate of rise seen in cortical surface imaging was still present for the resection margins that were positive for tumor compared to normal brain. Again, significant differences between the tumor and the normal brain existed for the rate of rise, peak optical change, and plateau 60 seconds after dye injection (all $p<0.01$). FIGS. 15–18 demonstrate that the inventive method and device can be used in combination with multiple injections of dye for repeated application throughout a tumor resection surgery (in this case, 4 separate injections of dye were given). Furthermore, extremely small islands of residual tumor can be mapped within the tumor margins.

Sensitivity and specificity of optical imaging was determined for 34 samples (n= 12 animals) Of 15 biopsy sites deemed negative for tumor by optical imaging, 14 of 15 were clear of tumor by histological analysis (sensitivity 93%). Most of the specimens that were negative for tumor were taken from the posterior wall of the tumor resection cavity or the depth of the cavity (where the hippicampus or denate gyrus were frequently biopsied). Of 19 biopsy sites deemed positive for tumor by optical imaging, 17 of the biopsy specimens were read as positive for tumor (specificity 89.5%). The two sites that were negative for tumor on histology but positive for tumor by optical imaging had increased cellularity but were deemed negative for tumor because there was no focus of tumor tissue present. The overall significance of these results are $p<0.001$.

Figure 19:
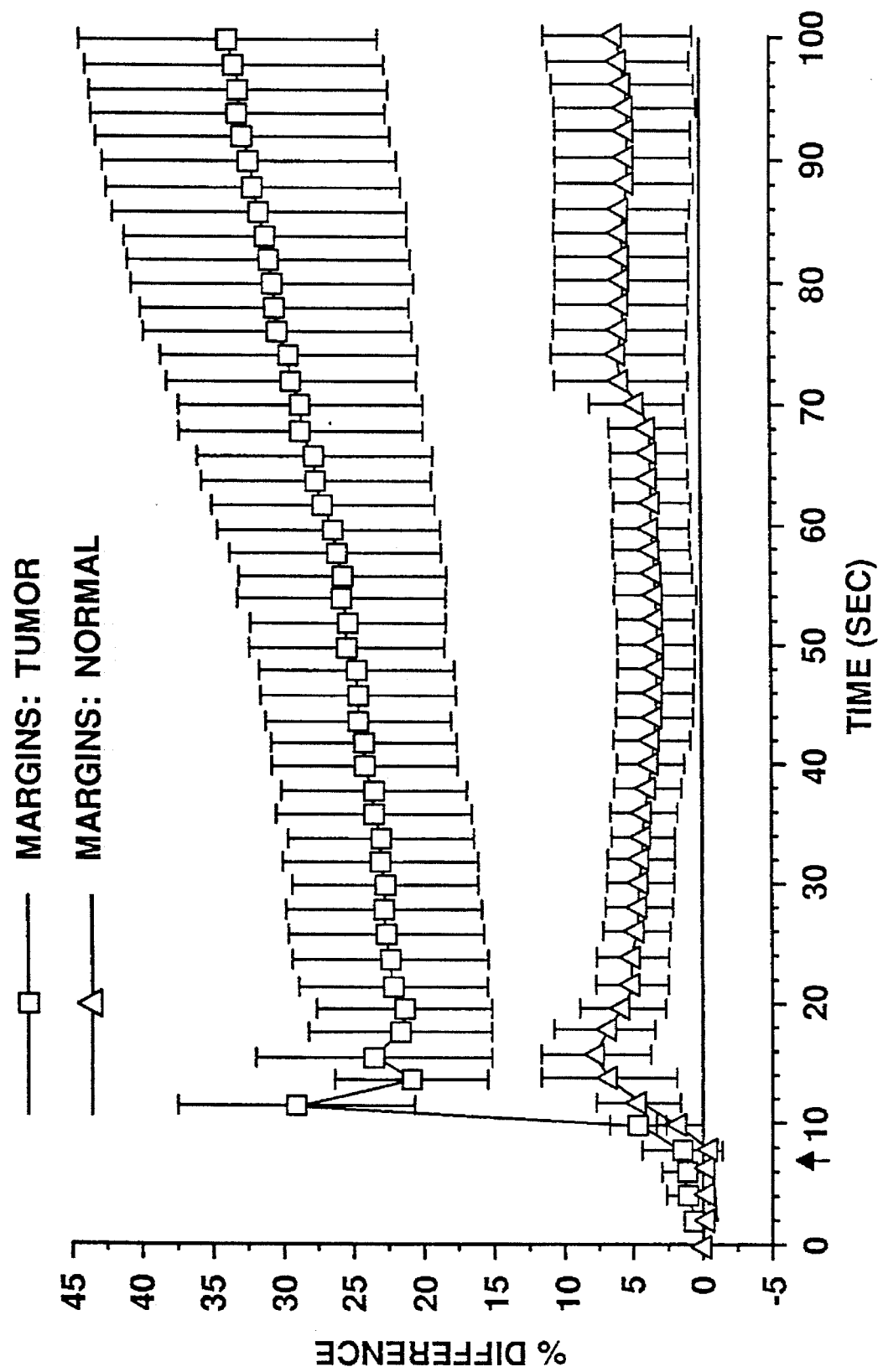
FIG. 19 shows dynamic information of dye uptake and clearance in tumor vs. non-tumor tissue. This is a plot of an average of the percentage change in emr absorption average over the spatial areas indicated by boxes 1 and 2 from FIG. 18A. The increase in absorption is a function of the concentration of dye in the tissue at a particular time. The graph labeled "margins tumor" is a plot of the dynamics of the absorption changes within box 1 from FIG. 18A. The graph labeled "margins normal" is a plot of the dynamics of the absorption changes within box 2 from FIG. 18A. This data as well as that from FIG. 18 show that the inventive device and method are able to distinguish tumor from non-tumor tissue within tumor margins with extremely high spatial and temporal resolution.

FIG. 19 shows dynamic information of dye uptake and clearance in tumor vs. non-tumor tissue. This is a plot of an average of the percentage change in emr absorption average over the spatial areas indicated by boxes 1 and 2 from FIG. 18A. The increase in absorption is a function of the concentration of dye in the tissue at a particular time. The graph labeled "margins tumor" is a plot of the dynamics of the absorption changes within box 1 from FIG. 19A. The graph labeled "margins normal" is a plot of the dynamics of the absorption changes within box 2 from FIG. 19A. This data as well as that from FIG. 19 show that the inventive device and method are able to distinguish tumor from non-tumor tissue within tumor margins with extremely high spatial and temporal resolution.

EXAMPLE 7

This example illustrates a series of experiments using a rat glioma model through an intact skull to investigate whether the inventive method and inventive device could function in to image tumor tissue through an intact skull and through intact skin prior to or after surgery. Far red wavelengths of emr are known to penetrate through bone and skin. Imaging of tumor tissue was attempted through the intact skull of the rat. The extent of tumor identified was not as accurate as with the cortex exposed, however, the area lying beneath the skull with tumor tissue was easily identified, localized and continued to concentrate dye after several minutes. Initially, after dye injection, the area of the tumor demonstrated a much larger signal than the normal brain of the contralateral hemisphere. One minute after dye injection, the dye had been cleared from the normal brain and the only residual signal remained in tumor tissue and the sagital/transverse sinuses.

FIG. 14 A is a gray-scale image of the cranial surface of a rat. The sagital suture runs down the center of the image. Tumor cells had been injected into the left side some days earlier so that this animal had developed a glioma on the left hemisphere of its brain. The right hemisphere was normal. Box 1 lays over the suspect region of brain tumor, and box 2 lays over normal tissue. FIG. 14B is a difference image 1 second after indocyanine green dye had been intravenously injected into the animal. The region containing tumor tissue becomes immediately visible through the intact cranium. FIG. 14C shows that 5 seconds after dye injection the dye can be seen to profuse through both normal and tumor tissue. FIG. 14D shows that 1 minute after dye injection, the normal tissue has cleared the dye, but dye is still retained in the tumor region. The concentration of dye in the center of this difference image is dye circulating in the sagital sinus.

Figure 15:
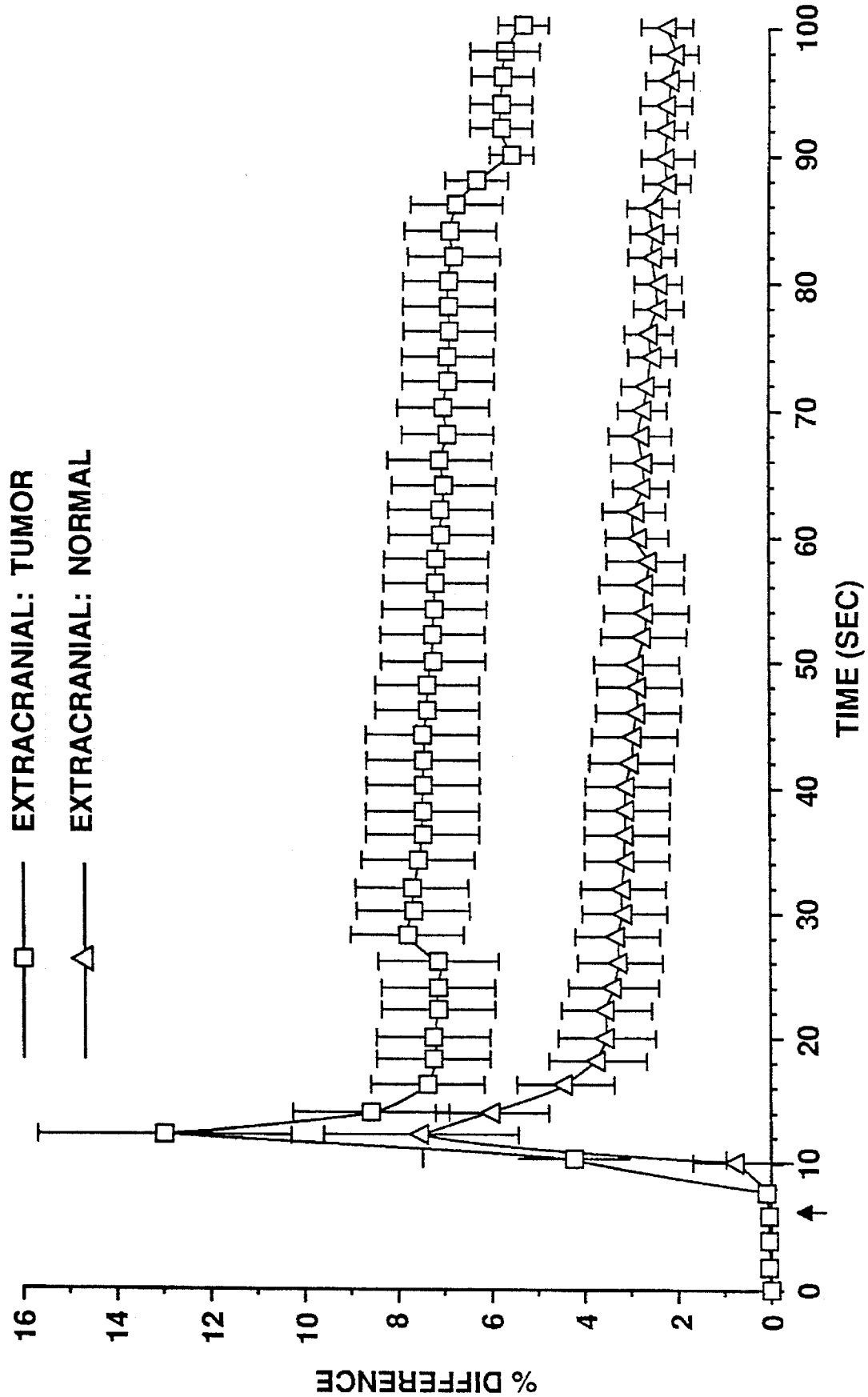
FIG. 15 illustrates dynamic information of dye uptake and clearance in tumor vs. non-tumor tissue through the intact skull. This is a plot of an average of the percentage change in emr absorption average over the spatial areas indicated by boxes 1 and 2 from FIG. 14A. The increase in absorption was a function of the concentration of dye in the tissue at a particular time. The graph labeled "extracranial tumor" is a plot of the dynamics of the absorption changes within box 1 from FIG. 14A. The graph labeled "extracranial: normal" is a plot of the dynamics of the absorption change within box 2 from FIG. 14 A.

The time course of optical changes imaged through the cranium from ten runs in four animals are shown in FIG. 15. The optical changes were determined by the average optical change in a box placed directly over the tumor and over the normal hemisphere. The increase in absorption is a function of the concentration of dye in the tissue at a particular time. The graph labeled "extracranial tumor" is a plot of the dynamics of the absorption changes within box 1 from FIG. 14A. The graph labeled "extracranial: normal" is a plot of the dynamics of the absorption change within box 2 from FIG. 14A. The peak optical changes for the tumor imaged through the cranium were 13.1±3.9% and this was significantly greater compared to normal brain of 7.8± 2.3% ($p<0.01$). The plateau phase 60 seconds after dye injection was also significantly greater in tumor tissue (40.5±9.6%) compared to normal brain (3.1±0.7%) ($p<0.01$).

EXAMPLE 8

This example illustrates a rat model showing activation of sensory cortex by stimulation of a peripheral nerve. More specifically, afferent sensory input was generated in an anesthetized rat by directly stimulating the sciatic nerve. In FIG. 5, the leftmost image is a gray-scale image of hind limb somatosensory cortex in an anesthetized rat. The magnification is sufficiently high so that individual capillaries can be distinguished (the smallest vessels visible in this image). The center image is an image of a percentage difference control optical image during rest. The magnitude of optical change is indicated by the gray-scale bar in the center of this image. The arrow beside this gray-scale indicates the direction of increasing amplitude. The rightmost image is a percentage difference map of the optical changes in the hind limb sensory cortex during stimulation of the sciatic nerve. Therefore, it is possible to utilize the inventive device and method to map functional areas of the cortex corresponding to different areas of the body.

EXAMPLE 9

Figure 13A:
FIG. 13A "shows the gray-scale image of the area of interest.
Figure 13B:
FIG. 13B shows the difference image prior to dye injection.
Figure 13C:
FIG. 13C' shows the area of interest 1 minute after intravenous dye injection.
Figure 13D:
FIG. 13D shows the area of interest 5 minutes after dye injection. Note that the dye is retained in this tissue for a significant time.
Figure 14A:
FIG. 14A is a gray-scale image of the cranial surface of a rat. The sagital suture runs down the center of the image. Tumor cells had been injected into the left side some days earlier so that this animal had developed a glioma on the left hemisphere of its brain. The right hemisphere was normal. Box 1 lays over the suspect region of brain tumor, and box 2 lays over normal tissue.
Figure 14B:
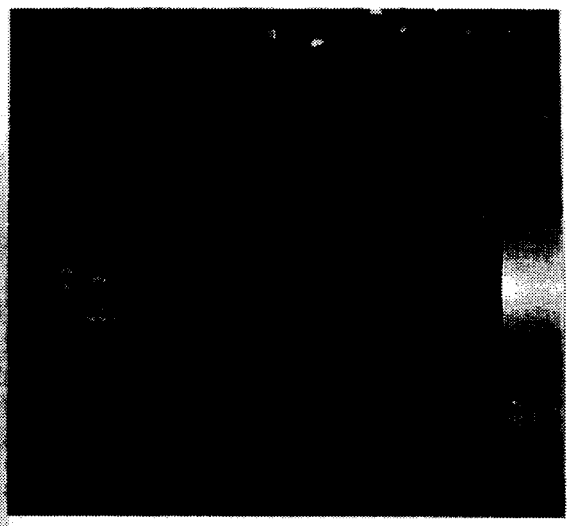
FIG. 14B vis a difference image 1 second after indocyanine green dye had been intravenously injected into the animal. The region containing tumor tissue became immediately visible through the intact cranium.
Figure 14C:
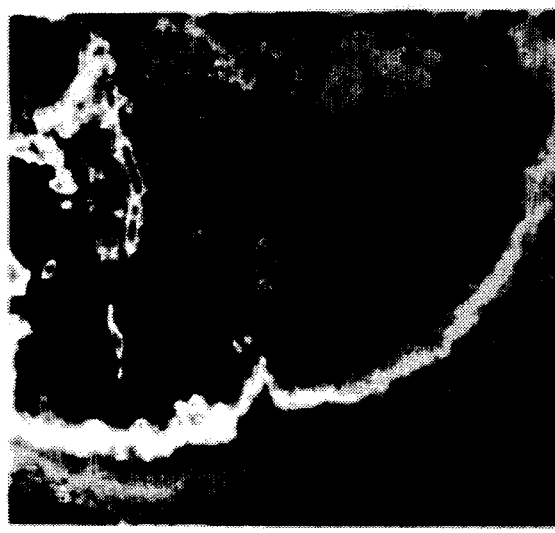
FIG. 14 shows non-invasive imaging of dye dynamics and identification of glioma through the intact cranium. This figure demonstrates that the invention can be used to identify tumors through the intact cranium.
FIG. 14D shows that 1 minute after dye injection, the normal tissue had cleared the dye, but dye was still retained in the tumor region. The concentration of dye in the center of this difference image was dye circulating in the sagital sinus.
Figure 14D:
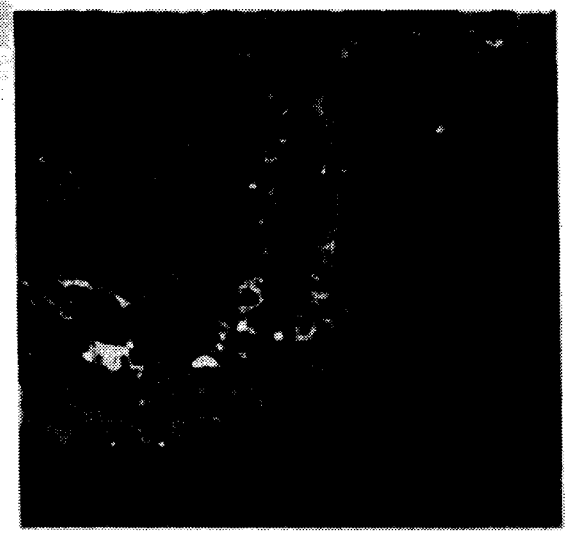

This example illustrates that differential dynamics of dye uptake and retention can characterize and identify tumor tissue in human patients that do not contrast enhance with traditional MRI imaging. A proportion of non-benign tumors are not observable with present MRI imaging techniques. The images in FIG. 13 are from a patient whose tumor did not contrast enhance with MRI. This lack of enhancement is usually typical of benign tumors. However, optical imaging was able to identify this tumor as a non-benign type (an anoplastic astrocytoma). FIG. 13 A shows the gray-scale image of the area of interest. FIG. 13 B shows the difference image prior to dye injection. FIG. 13C shows the area of interest 1 minute after intravenous dye injection, and FIG. 13D shows the area of interest 5 minutes after dye injection. Note that the dye is retained in this tissue for a significant time. As shown in FIGS. 10, 11, and 12, this dynamic trait is a characteristic of a non-benign tumor.

EXAMPLE 10

This example illustrates imaging of functional regions of peripheral nerves. A rat is anesthetised and dissected to expose the sciatic nerve. Using silver electrodes we electrically stimulate the caudal end of the nerve while acquiring a first sequence of difference images. We note the extent of the spread of the intrinsic optical changes in the nerve from the point of stimulation by examining the difference imaging containing the peak optical change from the control. Next, we make a crush in the nerve at a small distance anterior to the stimulating electrodes. We acquire a second sequence of difference images and compare the corresponding difference image from this sequence to the image containing the peak optical change from the first image. We note that the intrinsic optical changes diminish abruptly at the point where the nerve was damaged.

Finally, we stimulate the nerve anteriorly to where the crush was made and after acquiring a third sequence of difference images, we again note where the intrinsic changes abruptly end. This method allows us to localize the location and extent of damaged or disfunctional peripheral nerve tissue.

EXAMPLE 11

This example illustrates imaging of functional regions of Cranial Nerve VIII. Cranial nerve VIII (Vestibulocochlear nerve) is exposed. Sound tones provide the auditory stimulus which eventually cause activation of this nerve. A sequence of difference images before, during, and after the appropriate auditory stimuli are applied show that intrinsic optical changes of the nerve are associated with its functional activation. Next, a small region of this nerve is damaged by crushing. A second sequence of images reveal that auditory stimulation evokes intrinsic optical changes in the nerve up to the point of damage.

EXAMPLE 12

This example illustrates various methods for enhancing images obtained from tumor tissue or intrinsic signal difference images using multiple wavelength and/or laser illumination, and a method for extracting 3-D information using multiple wavelengths. We expose a region of cortex in an anesthised rat. First, illuminating with white light from a tungsten filament lamp, we acquire a sequence of difference images prior to, during, and following electrical stimulation of this region of cortex with bipolar stimulating electrodes. Next, we acquire second and third difference image sequences, following the identical procedure as we did for the first sequence, except that in the second sequence, the cortex is illuminated with with 690 nm and in the third sequence 510 nm light. The change in wavelengths is accomplished by placing 690±10 nm interference filter or a 510±10 nm interference filter between the lightsource and the brain.

We compute the contrast-enhanced image by first ratioing a control 690 nm image with a control 510 nm image. Second, we ratio a 690 nm image during stimulation with the corresponding 510 nm image. We then combine the ratio images to compute the percentage difference image. In this manner, the noise has been significantly reduced, hence the signal/noise ratio has been significantly increased.

Next, we show how to extract depth information from the multiple wavelength images that we have acquired. Longer wavelength light penetrates to a greater depth through the cortex, and shorter wavelength light to a lesser extent. Hence, the 690 nm image as penetrated cortex to x mm, and the 510 nm image to y mm where $x<y$.

We subtract the 610 nm image from the 510 nm image, showing an "optical wedge" containing information from a depth of $(x-y)$ mm to x mm within the cortical tissue. By using a series of other interence filters, we acquire a sequence of images containing information from many different depths of the cortex. It is possible to acquire 3-dimentional information.

Next, exposing tumor tissue in a rat in which we have induced tumor growth, we repeat all of the above experiments showing that in a like manner, we can improve signal/noise and extract 3-dimentional information in tumor tissue. However, instead of stimulating the tissue electrically, we inject the dyes indocyanine green or Evans blue.

Finally, we repeat the above experiments by illuminating the cortex at several different wavelengths with a dye-tunable laser (a coherent source) instead of with the non-coherent tungsten filament lamp. With the laser (or any coherent source) we have the additional advantage in that we can seperate out the components of the signal due to changes in reflection or scattering. By illuminating the cortex with the laser directly parallel to the camera (both of which are perpendicular to the brain), we are imaging reflected light only. By moving the laser at an angle $\theta$ to the camera, we are measuring changes due to scattering alone at this particular angle.

EXAMPLE 13

This example illustrates a C code to implement the inventive algorhithm and strategy for automatically translating a pair of images to the best fit with a control image with translation in the x-y plane. One can implement the algorithm so that the inventive device can automatically translate subsequently acquired images to the control image so that motion will be compensated in an on-line fashion in the operating room. As well, it is clear the this algorithm can be implemented in integer arithmetic so that it is computationally efficient. Also, since most of the memory required for this algorithm can be dynamically allocated, this algorithm makes efficient use of memory.

This program automatically translates two images stored in the Imaging Technology 151 frame buffers to a best fit according to which translation minimizes the variance of the subtracted images over the user-selected areas of interests. The user specifies an image for frame buffer B 1 and then specifies an image for frame buffer ALOW to be automatically translated to the B 1 image. If the number of areas of interest are less than 9 and the search depth is less than 8 then all the data can be read from the frame buffer into the host computer's RAM. This allows for speed and reduces the IO to the frame buffer. This program can be easily altered to use integer arithmetic only for all calculations.

This program is compilable under Microsoft's C/C++ Version 7.0 compiler linked with Imaging Technology's ITEX run-time library. It will run on a PC 486 compatible host computer controlling a 1k x 1k frame buffer, an ADI, and an ALU from Imaging Technology's ITEX 151 series hardware.
/*****************************************************************/

```c
#include <stdio.h>
#include <math.h>
#include <stdlib.h>
#include <conio.h>
#include <itex150.h>
#include <graph.h>
#include <float.h>
#include <dos.h>
#define MEM_CHUNK     20
#define QUIT          -1
#define GO            -2
#define RADIX_10      10
#define RETURN        13
#define ESC           27
#define CURSOR_UP     72
#define CURSOR_DOWN   80
#define CURSOR_RIGHT  77
#define CURSOR_LEFT   75
#define CURSOR_JUMP_UP    141
#define CURSOR_JUMP_DOWN  145
#define CURSOR_JUMP_RIGHT 116
#define CURSOR_JUMP_LEFT  115
struct data_box{
    int x, y;
    int height, width;
};
typedef struct data_box data_box;
int box_count = 0;
int depth = 10;
void init_box_overlay(void);
BYTE **ram_boxdata(data_box **map_ptr, int search_depth,int frame_buffer);
data_box **define_boxmap(void);
data_box *draw_boxes(void);
BYTE **diff_box(data_box **map_ptr, BYTE **fb1, BYTE **fb2,
         int box,int x_off, int y_off);
float sub_rects(data_box **map_ptr, BYTE **diff_rects, int search_depth,
         int ptr_place);
BYTE ***diff_map(data_box **map_ptr,int fb1, int fb2, int search_depth);
float *sum_rects(data_box **map_ptr, BYTE ***diff_rects, int search_depth
         ,int av_flag);
int *min_boxset(data_box **map_ptr, float *float_ptr, int search_depth);
float *var_rects(data_box **map_ptr, BYTE ***diff_rects, int search_depth,
```

```
        int av_flag);
data_box **define_boxmap(void) /* returns a pointer to an array of boxes */
{
    int i = 0, maxbox = MEM_CHUNK; /* dynamically allocate mem in 20-box */
    int error_flag = 0, inchar;     /*        chunks.        */
    data_box **group_of_boxes;
    data_box *box_pointer;
    int watch = GO;
    box_pointer = (data_box *)malloc(maxbox*sizeof(data_box));
        if(box_pointer == NULL)
            printf("\nTROUBLE AT 70\n");
    group_of_boxes = (data_box **)malloc(maxbox*sizeof(data_box *));
    if (group_of_boxes == NULL)
            printf("\nTROUBLE AT 74\n");            /* FLAG 1 !!! */
    else{
        while (watch != QUIT){
            if(error_flag == 0) {
                printf("\n\nType ESC use draw_boxes \n\n");
                inchar = getch();
                if (inchar == 0)
                    getch();
                if (ESC == inchar) {
                    box_count = 1;
                    init_box_overlay();
                    while( watch != QUIT) {
                      if (i >= maxbox) {
                         maxbox += MEM_CHUNK;
                         group_of_boxes = (data_box **)realloc(group_of_boxes,
                                          maxbox*sizeof(data_box *));
                         if (group_of_boxes == NULL)
                            printf("\nTROUBLE AT 91\n");;   /* FLAG 2 !!! */
                      }
                      group_of_boxes[i++] = draw_boxes();
                      printf("Do you want to draw box number %d ?\n",
                                       (box_count + 1));
                      inchar = getch();
                      if(inchar==0)
                           getch();
                      if (inchar == ESC)
                           box_count++;
                      else
                           watch = QUIT;
                    }
                }
            }
```

```c
            }
        }
        if(i < maxbox){
            group_of_boxes = (data_box **)realloc(group_of_boxes,
                                        (i)*sizeof(data_box *));
            if (group_of_boxes == NULL)
                printf("\nTROUBLE AT 113\n");
        }                   /* FLAG 3 !!!! */
        return(group_of_boxes);
}
/*********************
draw_boxes() is a simple function that draws boxes on the image for
the user to view using the overlay capabilities of the ITEX 151
ADI overlay capability. Its main function is to return a pointer
to data_box structure containg the information for the location and
area of the selected area of interest
******************************************/
int curs_x = 235, curs_y = 220;
data_box *draw_boxes(void)
{
  int dcurs_x,dcurs_y;
  int x_start, y_start, x_length, y_length;
  int text_char,k;
  char box_number[3];
  data_box *box_pointer;
  box_pointer = (data_box *)malloc(sizeof(data_box));
        if(box_pointer == NULL)
            printf("\nTROUBLE AT 131\n");
  line(B2,0,curs_x-4,curs_y,curs_x+4,curs_y,1);
  line(B2,0,curs_x,curs_y-5,curs_x,curs_y+5,1);
  adi_lutmode(DYNAMIC);
  k = 0;
  x_start = y_start = x_length = y_length = 0;
  while (1) {
     text_char=getch();
     if (text_char == RETURN) {
         ++k;
         dcurs_y=0;
         dcurs_x=0;
         if (k == 1) {
             x_start = curs_x;
             y_start = curs_y;
             line(B2,0,curs_x-4,curs_y,curs_x+4,curs_y,0);
             line(B2,0,curs_x,curs_y-5,curs_x,curs_y+5,0);
         }
```

```
            if (k == 2)
                break;
        }
        else if (text_char == 0){
            text_char = getch();
            switch(text_char) {
                case CURSOR_UP:
                    dcurs_y=-1;
                    dcurs_x=0;
                    break;
                case CURSOR_DOWN:
                    dcurs_y=1;
                    dcurs_x=0;
                    break;
                case CURSOR_LEFT:
                    dcurs_y=0;
                    dcurs_x=-1;
                    break;
                case CURSOR_RIGHT:
                    dcurs_y=0;
                    dcurs_x=1;
                    break;
                case CURSOR_JUMP_UP:
                    dcurs_y = -7;
                    dcurs_x = 0;
                    break;
                case CURSOR_JUMP_DOWN:
                    dcurs_y= 7;
                    dcurs_x = 0;
                    break;
                case CURSOR_JUMP_LEFT:
                    dcurs_y = 0;
                    dcurs_x = -7;
                    break;
                case CURSOR_JUMP_RIGHT:
                    dcurs_y = 0;
                    dcurs_x = 7;
                    break;
                default:
                    dcurs_x = 0;
                    dcurs_y = 0;
                    break;
            }
        }
        else
```

```
text_char = -1;
if ( (k == 0)&&(text_char != -1) ) {
    line(B2,0,curs_x-4,curs_y,curs_x+4,curs_y,0);
    line(B2,0,curs_x,curs_y-5,curs_x,curs_y+5,0);
    curs_x=max(min(curs_x+dcurs_x,511),0);
    curs_y=max(min(curs_y+dcurs_y,479),0);
    line(B2,0,curs_x-4,curs_y,curs_x+4,curs_y,1);
    line(B2,0,curs_x,curs_y-5,curs_x,curs_y+5,1);
}
else if (k == 1) {
    line(B2,0,x_start,y_start,x_start + x_length,y_start,0);
    line(B2,0,x_start,y_start,x_start,y_start + y_length,0);
    line(B2,0,x_start,y_start + y_length,x_start +
                        x_length,y_start + y_length,0);
    line(B2,0,x_start + x_length,y_start,x_start +
                        x_length,y_start + y_length,0);
    curs_x=max(min(curs_x+dcurs_x,511),0);
    curs_y=max(min(curs_y+dcurs_y,479),0);
    x_length = curs_x - x_start;
    y_length = curs_y - y_start;
    line(B2,0,x_start,y_start,x_start + x_length,y_start,1);
    line(B2,0,x_start,y_start,x_start,y_start + y_length,1);
    line(B2,0,x_start,y_start + y_length,x_start +
                        x_length,y_start + y_length,1);
    line(B2,0,x_start + x_length,y_start,x_start +
                        x_length,y_start + y_length,1);
    }
}
x_start = min(x_start,x_start + x_length);
y_start = min(y_start,y_start + y_length);
x_length = abs(x_length);
y_length = abs(y_length);
_itoa(box_count,box_number,RADIX_10);
if( (x_length < 10) || (y_length < 10) ) {
    if (x_length > y_length)
        text(B2,0,x_start+x_length/2-7,y_start-15,
                    HORIZONTAL,1,1,box_number);
    else{
        if(box_count < 10 )
            text(B2,0,x_start-11,y_start+y_length/2-2,
                        HORIZONTAL,1,1,box_number);
        else
            text(B2,0,x_start-18,y_start+y_length/2-2,
                        HORIZONTAL,1,1,box_number);
}
```

```
            }
            else
                text(B2,0,x_start+x_length/2-5,y_start+y_length/2-2,
                        HORIZONTAL,1,1,box_number);
 5          box_pointer->x = x_start;       /* x coordinate */
            box_pointer->y = y_start;       /* y coordinate */
            box_pointer->height = y_length;     /* vertical length */
            box_pointer->width = x_length;      /* horiz length */
            curs_x+=20;  /* move cross-hairs to nearby location */
10          curs_y+=20;
            return box_pointer;
        }
        void init_box_overlay(void)
        {                   /* Clear B2, set path to B1, and overlay */
15          fb_setsmask(FRAMEB,0x00FF);   /* B2 on B1                    */
            fb_clf(B2,0);
            select_path(B1);
            adi_hbanksel(1);
            adi_hgroupsel(RED);
20          adi_clearlut(250);
            adi_hgroupsel(GREEN);
            adi_clearlut(0);
            adi_hgroupsel(BLUE);
            adi_clearlut(0);
25      }
        void init_itex_stuff(void)
        {
          err_level(2);
          load_cfg("");
30        initsys();
        }
        BYTE **ram_boxdata(data_box **map_ptr,int search_depth, int frame_buffer){
            int i,j,k,x_start,x_end,x_length,y_start,y_length;
            BYTE **image_rects;
35          unsigned int count=0;
            unsigned int total_length=0;
            select_path(frame_buffer);
            for(i=0;i<box_count;i++)
                total_length += (*map_ptr[i]).width + 2*search_depth;
40          image_rects = (BYTE **)malloc(total_length*sizeof(BYTE *));
            if (image_rects == NULL)
                printf("\n409\n");
            for(i=0;i<box_count;i++){
                x_start = (*map_ptr[i]).x - search_depth;
45              x_end =  (*map_ptr[i]).x + search_depth + (*map_ptr[i]).width;
```

```
            x_length = (*map_ptr[i]).width + 2*search_depth;
            y_start = (*map_ptr[i]).y - search_depth;
            y_length = (*map_ptr[i]).height + 2*search_depth;
            for(j = x_start;j < x_end; j++){
                image_rects[count] = (BYTE *)malloc(sizeof(BYTE)*y_length);
                if (image_rects[count] == NULL)
                    printf("\nSCREWUP 420\n");
                fb_rvline(B1,j,y_start,y_length,image_rects[count]);
                count++;
            }
        }
        return(image_rects);
    }
    BYTE **diff_box(data_box **map_ptr, BYTE **fb_ptr1, BYTE **fb_ptr2,
                    int box_number,int x_off, int y_off){
        unsigned int x_length, y_length;
        static unsigned int count1=0,count2=0;
        int i,j;
        static int old_number;
        BYTE **box;
        x_length = (*map_ptr[box_number]).width;
        y_length = (*map_ptr[box_number]).height;
        if (box_number == 0)
            old_number = 0;
        if (old_number != box_number){
            count1 += x_length;
            count2 += x_length + 2*depth;
            old_number = box_number;
        }
        box = (BYTE **)malloc(sizeof(BYTE *)*x_length);
        if(box == NULL)
            printf("\nScrewed at line 341 \n");
        for(i=0;i<x_length;i++){
            box[i] = (BYTE *)malloc(sizeof(BYTE)*y_length);
            if (box[i] == NULL)
                printf("\nScrewed at 362\n");
            for(j=0;j<y_length;j++)
                box[i][j] = (BYTE)( abs((int)(fb_ptr1[i+count1][j]) -
                                        (int)(fb_ptr2[i+x_off+count2][j+y_off]) ) );
        }
        return(box);
    }
    BYTE ***diff_map(data_box **map_ptr,int fb1, int fb2, int search_depth){
        BYTE ***diff_rects,data_box, **fb1_ptr, **fb2_ptr;
        int count= 0;
```

```
    int i,j,k,l;
    unsigned int size, total_size = box_count*(2*search_depth + 1)*
                                    (2*search_depth + 1);
    size = 2*search_depth + 1;
5   diff_rects = (BYTE ***)malloc(sizeof(BYTE **)*total_size);
    if (diff_rects == NULL)
      printf("\nScrewed at 379\n");
    fb1_ptr = ram_boxdata(map_ptr,0,fb1);
    fb2_ptr = ram_boxdata(map_ptr,search_depth,fb2);
10  for(i=0;i<box_count;i++)
      for(j=0;j<size;j++)
        for(k = 0;k<size;k++){
          diff_rects[count] = diff_box(map_ptr,fb1_ptr,fb2_ptr,i,j,k);
          count++;
15      }
    return(diff_rects);
    }
    float *sum_rects(data_box **map_ptr, BYTE ***diff_rects, int search_depth,
                    int av_flag){
20  unsigned int i,j,k,l,m,count=0;
    float size = (2*search_depth + 1);
    float total_size = (2*search_depth + 1)*(2*search_depth + 1)*box_count;
    float *sum_ptr;
      sum_ptr = (float *)calloc((unsigned int)total_size,sizeof(float));
25    if (sum_ptr == NULL)
        printf("\nSCREWUP AT 537\n");
      for(i=0;i<box_count;i++)
        for (j=0;j<size;j++)
          for(k=0;k<size;k++){
30          for(l=0;l < (*map_ptr[i]).width; l++)
              for(m=0;m < (*map_ptr[i]).height;m++)
                sum_ptr[count] += diff_rects[count][l][m];
            if(av_flag == ON)
              sum_ptr[count] = sum_ptr[count]/
35                           ((*map_ptr[i]).width * (*map_ptr[i]).height);
            count++;
          }
      return(sum_ptr);
    }
40  float *var_rects(data_box **map_ptr, BYTE ***diff_rects, int search_depth,
                    int av_flag){
    unsigned int i,j,k,l,m,count=0;
    float size = (2*search_depth + 1);
    float total_size = (2*search_depth + 1)*(2*search_depth + 1)*box_count;
45  float *var_ptr,*av_ptr;
```

```
                av_ptr = sum_rects(map_ptr,diff_rects,search_depth,av_flag);
                    var_ptr = (float *)calloc((unsigned int)total_size,sizeof(float));
                    if(var_ptr == NULL)
                        printf("\nTrouble at 477\n");
 5              for(i=0;i<box_count;i++)
                    for (j=0;j<size;j++)
                        for(k=0;k<size;k++){
                            for(l=0;l < (*map_ptr[i]).width; l++)
                                for(m=0;m < (*map_ptr[i]).height;m++)
10                                  var_ptr[count] += ((float)(diff_rects[count][l][m])
                                        - av_ptr[count])*((float)(diff_rects[count][l][m])
                                                - av_ptr[count]);
                            count++;
                        }
15              free(av_ptr);
                return(var_ptr);
            }
            int *min_boxset(data_box **map_ptr, float *float_ptr,int search_depth){
                unsigned int i,j,box_jump;
20              float metric,min_metric = FLT_MAX,position=0;
                int shift[3];
                div_t div_result;
                box_jump = (2*search_depth + 1)*(2*search_depth + 1);
                for(i=0;i<box_jump;i++){
25                  metric = 0;
                    for(j=0;j<box_count;j++)
                        metric += float_ptr[j*box_jump + i];
                    if(metric < min_metric){
                        min_metric = metric;
30                      position = i;
                    }
                }
                div_result = div((int)position,(int)(2*search_depth + 1));
                shift[0] = (int)position;
35              shift[1] = depth - div_result.quot;
                shift[2] = depth - div_result.rem;
                return(shift);
            }
            int main(void)
40          {
                BYTE ***mock_pointer;
                char image[12];
                data_box **map_pointer;
                int *stats_ptr,i;
45              float *sum_ptr3;
```

```c
         int *trans3;
         init_itex_stuff();
         fb_init();
         _clearscreen( _GCLEARSCREEN );
5        _settextposition( 10, 10);
         select_path(B1);
         _outtext("BASE Image : ");
         scanf("%s", image);
         im_read(B1,0,0,512,480,image);
10       _settextposition( 15, 10);
         select_path(ALOW);
         _outtext("Image to translate : ");
         scanf("%s", image);
         im_read(ALOW,0,0,512,480,image);
15       _settextposition(20,20);
         _outtext("Search depth: ");
         scanf("%d",&depth);
         select_path(B1);
         map_pointer = define_boxmap();
20       sum_ptr3 = var_rects(map_pointer,mock_pointer,depth,ON);
         trans3 = min_boxset(map_pointer,sum_ptr3,depth);
         printf("\nVARIANCE : pos = %d, x_trans = %d, y_trans = %d\n",
                   trans3[0],trans3[1],trans3[2]);
         free(mock_pointer);
25       free(sum_ptr3);
         free(trans3);
         return 0; }
```

What is claimed is:

1. A method for imaging tumor tissue adjacent to nerve tissue to aid in selective resection of tumor tissue without destroying nerve tissue, comprising:
   (a) illuminating an area of interest with a source of electromagnetic radiation (emr) containing wavelengths of emr absorbed by a dye;
   (b) obtaining a video signal of the area of interest as a series of frames and processing the series of frames into an averaged control image;
   (c) stimulating the nerve with an appropriate paradigm to activate the nerve;
   (d) obtaining a nerve subsequent series of frames at the time of stimulation and processing the nerve subsequent series of frames into a nerve subsequent averaged image;
   (e) obtaining a nerve difference image by subtracting the averaged control image from the nerve subsequent averaged image to image the active nerve;
   (f) administering the dye into vasculature perfusing the area of interest;
   (g) obtaining a tumor subsequent series of frames and processing the tumor subsequent series of frames into a tumor subsequent averaged image; and
   (h) obtaining a tumor difference image by subtracting the averaged control image from the tumor subsequent averaged image to visualize the tumor.

2. The method for imaging tumor tissue adjacent to nerve tissue of claim 1, wherein the tumor difference image and the nerve difference image are superimposed upon each other to simultaneously visualize the relative locations of the tumor tissue and the nerve tissue.

3. The method of claim 1 wherein the dye is selected from the group consisting of indocyanine green, hematoporphyrin, fluorescein, fluorescamine, $NPe_6$, BPD, Evans Blue, and combinations thereof.

4. The method of claim 1 wherein the source of emr is selected from the group consisting of high intensity light, diffuse or uniform visible light, infrared emr, and combinations thereof.

* * * * *